(12) United States Patent
Kaplan et al.

(10) Patent No.: US 9,173,910 B2
(45) Date of Patent: Nov. 3, 2015

(54) COMPOSITIONS OF MICROBIOTA AND METHODS RELATED THERETO

(71) Applicants: Ethicon Endo-Surgery, Inc., Cincinnati, OH (US); The General Hospital Corporation, Boston, MA (US)

(72) Inventors: Lee M. Kaplan, Wellesley, MA (US); Alice P. Liou, Charlestown, MA (US); Peter J. Turnbaugh, Somerville, MA (US); Jason L. Harris, Mason, OH (US)

(73) Assignees: The General Hospital Corporation, Boston, MA (US); Ethicon Endo-Surgery, Inc., Cincinnati, OH (US); President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 13/780,284

(22) Filed: Feb. 28, 2013

(65) Prior Publication Data

US 2013/0224155 A1    Aug. 29, 2013

Related U.S. Application Data

(60) Provisional application No. 61/604,824, filed on Feb. 29, 2012.

(51) Int. Cl.
*A61K 35/74* (2015.01)
*A61K 35/741* (2015.01)
*A61K 45/06* (2006.01)
*C12Q 1/68* (2006.01)

(52) U.S. Cl.
CPC ............... *A61K 35/741* (2013.01); *A61K 45/06* (2013.01); *C12Q 1/689* (2013.01)

(58) Field of Classification Search
None
See application file for complete search history.

(56) References Cited

U.S. PATENT DOCUMENTS

| 2010/0087481 | A1* | 4/2010 | Lee ................................ 514/312 |
| 2010/0172874 | A1 | 7/2010 | Turnbaugh et al. |
| 2011/0280840 | A1* | 11/2011 | Blaser et al. ................. 424/93.4 |
| 2012/0165792 | A1 | 6/2012 | Ortiz et al. |

OTHER PUBLICATIONS

Navarro-Noya, Y.E., Jan-Roblero, J., del Carmen Gonzalez-Chavez, M., Hernandez-Gama, R., and Hernandez-Rodriguez, C. "Bacterial communities associated with the rhizosphere of pioneer plants (*Bahia xylopoda* and *Viguiera linearis*) growing on heavy metals-contaminated soils", Antonie van Leeuwenhoek 2010, vol. 97, pp. 335-349.*

Derrien, M., Van Baarlen, P., Hooiveld, G., Norin, E., Muller, M., and de Vos, W.M. "Modulation of mucosal immune response, tolerance, and proliferation in mice colonized by the mucin-degrader *Akkermansia muciniphila*", Frontiers in Microbiology, EPub 2011, vol. 2, pp. 1-14.*

Kootte, R.S., Vrieze, A., Holleman, F., Dallinga-Thie, G.M., Zoetendal, E.G., de Vos, W.M., Groen, A.K., Hoekstra, J.B.L., Stroes, E.S., and Nieuwdorp, M. "The therapeutic potential of manipulating gut microbiota in obesity and type 2 diabetes mellitus", Diabetes, Obesity and Metabolism, EPub 2011, vol. 14, pp. 112-120.*

Hosseini, E., Grootaert, C., Verstraete, W., and Van de Wiele, T. "Propionate as a health-promoting microbial metabolite in the human gut", Nutrition Reviews 2010, vol. 69, pp. 245-258.*

Yoon, M. "The role of PPARalpha in lipid metabolism and obesity: Focusing on the effects of estrogen on PPARalpha actions", Pharmacological Research 2009, vol. 60, pp. 151-159.*

Backhed et al., Mechanisms underlying the resistance to diet-induced obesity in germ-free mice. Proc Natl Acad Sci USA, 2007. 104(3): p. 979-84.

Backhed et al., The gut microbiota as an environmental factor that regulates fat storage. Proc Nat Acad Sci US A, 2004. 101(44): p. 15718-23.

Cani et al., Changes in gut microbia control metabolic endotoxemia-induced inflammation in high-fat diet-induced obesity and diabetes in mice. Diabetes, 2008. 57(6): p. 1470-81.

Cani et al., Metabolic endotoxemia initiates obesity and insulin resistance. Diabetes, 2007. 56(7): p. 1761-72.

De Filippo et al., Impact of diet in shaping gut microbiota revealed by a comparative study in children from Europe and rural Africa. Proc Nat Acad Sci US A, 2010. 107(33): p. 14691-6.

Furet et al., Differential Adaptation of Human Gut Microbiota to Bariatric Surgery-Induced Weight Loss: Links with Metabolic and Low-Grade Inflammation Markers. Diabetes, 2010; 59(12):3049-3057.

Hildebrandt et al., High-fat diet determines the composition of the murine gut microbiome independently of obesity. Gastroenterology, 2009. 137(5): p. 1716-24 e1-2.

International Search Report and Written Opinion for Application No. PCT/US2013/28271, mailed May 13, 2013. 17 pages.

(Continued)

*Primary Examiner* — Allison Fox
*Assistant Examiner* — Michelle F Paguio Frising
(74) *Attorney, Agent, or Firm* — Mintz Levin Cohn Ferris Glovsky and Popeo, P.C.; William C. Geary; Shovon Ashraf

(57) ABSTRACT

Methods and compositions are provided for treating weight related conditions and metabolic disorders by altering microbiota in a subject. One aspect provides methods and compositions to alter microbiota in a subject by administering to the subject a composition that includes a substantially purified microbiota from phyla such as Bacteroidetes, Proteobacteria, Firmicutes and Verrucomicrobia or orders such as Bacteroidales, Verrucomicrobiales, Clostridiales and Enterobacteriales or genera such as *Alistipes, Clostridium, Escherichia*, and *Akkermansia*. Another aspect includes a pharmaceutical composition for altering microbiota that includes a therapeutically effective amount of substantially purified microbiota and a pharmaceutically acceptable carrier. Yet another aspect includes methods for treating a disorder, such as obesity, in a subject in need of such treatment by changing relative abundance of microbiota in a gastrointestinal tract of the subject without or in addition to a surgical procedure.

29 Claims, 27 Drawing Sheets

(56) References Cited

OTHER PUBLICATIONS

Lefebvre et al., Role of bile acids and bile acid receptors in metabolic regulation. Physiol Rev, 2009. 89(1): p. 147-91.

Ley et al., Microbial ecology: human gut microbes associated with obesity. Nature, 2006. 444(7122): p. 1022-3.

Ley et al., Obesity alters gut microbial ecology. Proc Nat Acad Sci U S A, 2005. 102(31): p. 11070-5.

Li et al., Metabolic surgery profoundly influences gut microbial-host metabolic cross-talk. Gut, 2011; 60:1214-1223.

Patti et al., Serum bile acids are higher in humans with prior gastric bypass: potential contribution to improved glucose and lipid metabolism. Obesity (Silver Spring), 2009. 17(9): p. 1671-7.

Rubino et al., Metabolic surgery to treat type 2 diabetes: clinical outcomes and mechanisms of action. Annu Rev Med. 2010;61:393-411.

Samuel et al., A humanized gnotobiotic mouse model of host-archaeal-bacterial; mutualism. Proc Natl Acad Sci US A, 2006. 103(26): p. 10011-6.

Speakman et al., Revised equations for calculating CO2 production from doubly labeled water in humans. Am J Physiol. Jun. 1993;264(6 Pt 1):E912-7.

Stylopoulos et al., Roux-en-Y gastric bypass enhances energy expenditure and extends lifespan in diet-induced obese rats. Obesity (Silver Spring), 2009. 17(10): p. 1839-47.

Swann et al., Systemic gut microbial modulation of bile acid metabolism in host tissue compartments. Proc Natl Acad Sci US A. 2011;108 Suppl 1: p. 4523-30.

Thaler at al., Minireview: Hormonal and metabolic mechanisms of diabetes remission after gastrointestinal surgery. Endocrinology, 2009. 150(6): p. 2518-25.

Thomas et al., TGR5—mediated bile acid sensing controls glucose homeostasis. Cell Metab, 2009. 10(3): p. 167-77.

Turnbaugh et al., A core gut microbiome in obese and lean twins. Nature, 2009.; 457(7228): p. 480-4.

Turnbaugh et al., An obesity-associated gut microbiome with increased capacity for energy harvest. Nature, 2006. 444(7122): p. 1027-31.

Turnbaugh et al., The effect of diet on the human gut microbiome: a metagenomic analysis in humanized gnotobiotic mice. Sci Transl Med, 2009. 1(6): p. 6ra14.

Watanabe et al., Bile acids induce energy expenditure by promoting intracellular thyroid hormone activation. Nature, 2006. 439(7075): p. 484-9.

Zhang et al., Human gut microbiota in obesity and after gastric bypass. Proc Natl Acad Sci U S A. Feb. 17, 2009;106(7):2365-70. doi: 10.1073/pnas.0812600106. Epub Jan. 21, 2009.

\* cited by examiner

*P<0.05, ***P<0.001

***P<0.001

* P < 0.05

* P < 0.05, **P<0.01

*P < 0.05

*P < 0.05, **P<0.01

*P<0.05, **P<0.01

COMPOSITIONS OF MICROBIOTA AND METHODS RELATED THERETO

CROSS REFERENCE TO RELATED APPLICATIONS

The present application claims the priority of U.S. Provisional Application Ser. No. 61/604,824 filed Feb. 29, 2012, entitled "Compositions of Microbiota and Methods Related Thereto," which is hereby incorporated by reference in its entirety.

FIELD OF THE INVENTION

The present invention relates to methods and compositions involving microbiota for weight loss and the treatment of metabolic disease and its comorbidities, such as obesity, type II diabetes mellitus, etc.

BACKGROUND OF THE INVENTION

Obesity is a comorbidity of metabolic disease and represents the most prevalent of body weight disorders, and it is the most important nutritional disorder in the Western world, with estimates of its prevalence ranging from 30% to 50% of the middle-aged population. The number of overweight (defined as a person with a body mass index (BMI) equal to or greater than 25 kg/m$^2$) and obese (defined as a person with a BMI equal to or greater than 30 kg/m$^2$) Americans has continued to increase since 1960, a trend that is not slowing down. Today, approximately 64.5% of adult Americans (about 199 million) are categorized as being overweight or obese. Obesity is becoming a growing concern as the number of people with obesity continues to increase and more is learned about the negative health effects of obesity. Each year, obesity causes at least 300,000 deaths in the U.S., and healthcare costs of American adults with obesity amount to more than $147 billion (Centers for Disease Control and Prevention). Severe obesity, in which a person has a BMI equal to or greater than 35, in particular poses significant risks for severe health problems. Even mild obesity increases the risk for premature death, diabetes, hypertension, atherosclerosis, gallbladder disease and certain types of cancer. Because of its high prevalence and significant health consequences, its treatment should be a high public health priority. Reductions in weight as little as 5% of a patient's total body weight are associated with significant improvements in comorbidities associated with obesity and metabolic disease such as type II diabetes mellitus, hypertension, hyperlipidemia, obstructive sleep apnea, gastroesophageal reflux disease, breathing difficulties, etc. Accordingly, a great deal of attention is being focused on treating patients with various stages of obesity.

Surgical procedures to treat severe obesity and the associated comorbidities have included various forms of gastric and intestinal bypasses (stomach stapling), biliopancreatic diversion, adjustable gastric banding, vertical banded gastroplasty, gastric plications, and sleeve gastrectomies (removal of all or a portion of the stomach). Although these procedures can be performed using traditional open surgical techniques, such surgical procedures have increasingly been performed laparoscopically. Reduced postoperative recovery time, markedly decreased post-operative pain and wound infection, and improved cosmetic outcome are well established benefits of laparoscopic surgery, derived mainly from the ability of laparoscopic surgeons to perform an operation utilizing smaller incisions of the body cavity wall. However, such surgical procedures risk a variety of complications during surgery, pose undesirable post-operative consequences such as pain and cosmetic scarring, and often require lengthy periods of patient recovery, particularly in the obese patient. Patients with obesity thus rarely seek or accept surgical intervention, with less than about 1% of patients with obesity being surgically treated for this disorder. Furthermore, even if successfully performed and initial weight loss occurs, surgical intervention to treat obesity may not result in lasting weight loss or improvements in comorbid conditions, thereby indicating a patient's need for additional, different, supplemental or complementary obesity treatment(s).

Nonsurgical methods for treating obesity have also been developed. However, effective therapies for increasing energy expenditure leading to improvements in metabolic outcomes, e.g., decreasing food intake, weight loss, glucose metabolism etc., have focused on pharmaceutical approaches, which have various technical and physiological limitations.

Accordingly, there remains a need for new methods and compositions for weight loss and treating metabolic disorders, such as obesity.

SUMMARY OF THE INVENTION

The present invention generally provides methods and compositions for treating weight related conditions and disorders by altering microbiota in a subject. One aspect provides methods and compositions to alter microbiota in a subject by administering to the subject a composition that includes a substantially purified microbiota from phyla such as Bacteroidetes, Proteobacteria, Firmicutes and Verrucomicrobia or orders such as Bacteroidales, Enterobacteriales, Clostridiales, and Verrucomicrobiales, or genera such as *Alistipes, Escherichia, Clostridium*, or *Akkermansia*. Another aspect provides a pharmaceutical composition for altering microbiota that includes a therapeutically effective amount of substantially purified microbiota from phyla such as Bacteroidetes, Proteobacteria, Firmicutes and Verrucomicrobia or orders such as Bacteroidales, Enterobacteriales, Clostridiales, and Verrucomicrobiales or genera such as *Alistipes, Escherichia, Clostridium*, or *Akkermansia*, and a pharmaceutically acceptable carrier. Methods for treating a disorder or condition associated with weight gain or methods for weight loss in a subject in need of such treatment by substantially increasing a relative abundance of microbiota from phyla such as Bacteroidetes, Proteobacteria, Firmicutes and Verrucomicrobia or orders such as Bacteroidales, Enterobacteriales, Clostridiales, and Verrucomicrobiales or genera such as *Alistipes, Escherichia, Clostridium*, or *Akkermansia* in a gastrointestinal tract of the subject without, or in addition to, a surgical procedure are also disclosed.

One aspect provides methods and compositions to alter microbiota by administering one or more of a)-i) as follows: a) substantially purified Verrucomicrobia; b) substantially purified Enterobacteriales; c) substantially purified Bacteroidales; d) substantially purified Clostridiales; e) substantially purified *Alistipes*; f) substantially purified *Clostridium*; g) substantially purified *Akkermansia*; h) substantially purified *Escherichia*; and i) a compound that when administered to a subject increases a relative abundance of at least one of Verrucomicrobia, Verrucomicrobiales, Enterobacteriales, Bacteroidales, and Clostridiales in the subject and/or decreases a relative abundance of Tenericutes or Erysipelotrichales in the subject. In some embodiments, the methods and compositions can optionally include administering one or more of a) a compound that when administered to a subject alters a relative abundance of at least one of Bacteroidetes, Verrucomicrobia, Firmicutes, Tenericutes and Proteobacteria; b) substantially purified Bacteroidetes; c) substantially purified Proteobacteria; d) substantially purified Firmicutes; and e) substantially purified Verrucomicrobia. The term "at least one of" as used throughout should be understood to include at least two of, at least three of, at least four of, etc.

Another aspect provides methods and compositions to alter microbiota by decreasing a relative abundance of Firmicutes or Tenericutes. In an exemplary embodiment, the relative abundance of Firmicutes or Tenericutes in the subject can be decreased by at least about 5%. In a particular embodiment, the relative abundance of either Erysipelotrichales, *Lactobacillus*, or *Allobaculum*, or combinations thereof, in the subject can be decreased by, for example, at least about 5%.

A further aspect provides methods to alter microbiota in a subject by administering to the subject a composition that includes a substantially purified Verrucomicrobia, a substantially purified Enterobacteriales, a substantially purified Bacteroidales and/or a substantially purified Clostridiales to treat a disorder selected from obesity, metabolic syndrome, insulin deficiency, insulin-resistance related disorders, glucose intolerance, diabetes, non-alcoholic fatty liver, and abnormal lipid metabolism is disclosed. The compositions can include at least one of substantially purified Verrucomicrobia, a substantially purified Enterobacteriales, a substantially purified Bacteroidales and/or a substantially purified Clostridiales that is a live bacterial strain. The methods can also include increasing a relative abundance of phyla such as Bacteroidetes, Proteobacteria, Firmicutes and Verrucomicrobia or orders such as Bacteroidales, Enterobacteriales, Clostridiales, and Verrucomicrobiales or genera such as *Alistipes, Escherichia, Clostridium*, or *Akkermansia* in the subject (e.g. by at least about 5%).

The methods disclosed can further include delivering the composition to a target location within the subject. In one embodiment, the composition can be directly delivered to at least a stomach, a small intestine, and a large intestine of the subject. The composition can also be formulated for oral delivery.

The method can also include administering an osmotic laxative and/or an antibiotic to the subject and/or performing a surgical procedure selected from gastric bypass, duodenojejunal bypass, biliopancreatic diversion, vertical sleeve gastrectomy, adjustable gastric banding, vertical banded gastroplasty, intragastric balloon therapy, gastric plication, Magenstrasse and Mill, small bowel transposition, biliary diversion, duodenal endoluminal barrier, similar manipulations of the gastrointestinal tract, and other gastrointestinal bariatric and metabolic procedures.

Another aspect includes a pharmaceutical or another composition for altering microbiota that includes a therapeutically effective amount of substantially purified microbiota from one or more phyla such as Bacteroidetes, Proteobacteria, Firmicutes and Verrucomicrobia or orders such as Bacteroidales, Enterobacteriales, Clostridiales and Verrucomicrobiales or genera such as *Alistipes, Escherichia, Clostridium*, or *Akkermansia* and a pharmaceutically acceptable carrier. In other embodiments, a therapeutically effective amount of such compositions can be contained in food, drink, dietary supplement, and/or food additive to be consumed by a subject.

Yet another aspect includes methods for treating obesity in a subject in need of such treatment by substantially increasing a relative abundance of at least one of Verrucomicrobiales, Enterobacteriales, Bacteroidales, and Clostridiales in a gastrointestinal tract of the subject without or in addition to a surgical procedure.

The methods can also include administering an additional agent, such as an antibiotic and/or an osmotic laxative, to the subject before, concurrent with, and/or after administration of the composition.

An additional aspect includes a kit for measuring the relative abundance of Tenericutes, Mollicutes, Verrucomicrobiales, Enterobacteriales, Bacteroidales, and/or Clostridiales in a sample. The kit can include at least a pair of primers that hybridize to Tenericutes, Mollicutes, Verrucomicrobiales, Enterobacteriales, Bacteroidales or Clostridiales nucleic acids and hybridization reagents.

A further aspect provides a method of altering microbiota in a subject by administering a composition to the subject thereby altering microbiota in the subject so that the microbiota mimics the microbiota found in a subject responsive to a gastric bypass or other gastrointestinal bariatric or metabolic procedure.

BRIEF DESCRIPTION OF THE DRAWINGS

The invention will be more fully understood from the following detailed description taken in conjunction with the accompanying drawings, in which.

DETAILED DESCRIPTION OF THE INVENTION

Figure 1:
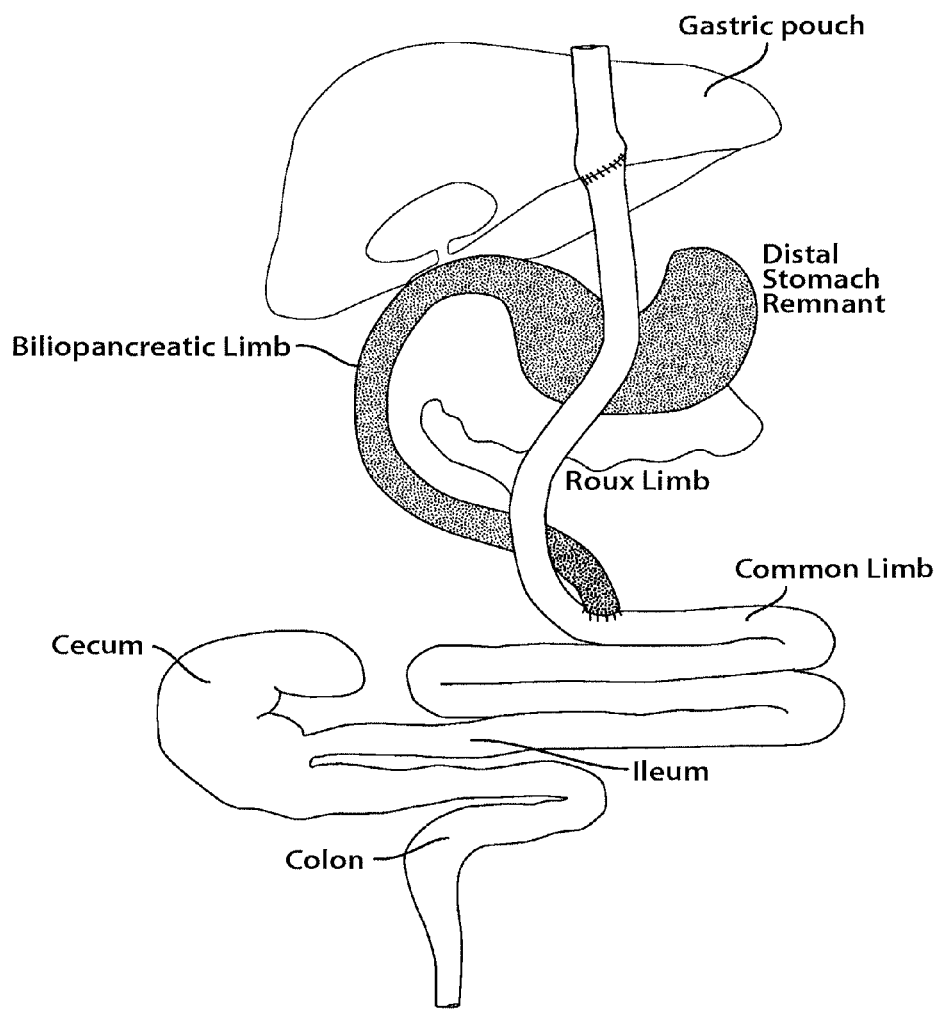
FIG. 1 is a diagram of the gastrointestinal anatomy after Roux en-Y Gastric Bypass.

Certain exemplary embodiments will now be described to provide an overall understanding of the principles of the structure, function, manufacture, and use of the therapeutics and methods disclosed herein. One or more examples of these embodiments are illustrated in the accompanying drawings. Those skilled in the art will understand that the therapeutics and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

All publications, patents and patent applications cited herein are hereby incorporated by reference in their entirety. As used in this specification and the appended claims, the singular forms "a," "an," and "the" include plural references unless the content clearly dictates otherwise. The terms used in this invention adhere to standard definitions generally accepted by those having ordinary skill in the art.

Studies show that the relationship between gut microbiota and humans is not merely commensal (a non-harmful coexistence), but rather often is a mutualistic, symbiotic relationship. Although animals can survive with no gut microbiota, the microorganisms perform a host of useful functions, such as stimulating immune development, preventing invasion by pathogenic bacteria, regulating the development of the gut, fermenting unused dietary substrates, metabolism of glycans and amino acids, synthesis of vitamins (such as biotin and vitamin K) and isoprenoids, biotransformation of xenobiotics, and directing the host to store fats. It is therefore believed that changes in the composition of the gut microbiota could have important health effects.

Indeed, it has been discovered that a correlation between weight loss due to surgical intervention, such as gastric bypass, and gut microbiota has been observed. Therefore, the invention disclosed is generally directed to therapeutic methods for weight loss and compositions for treating disorders and conditions associated with weight gain, such as obesity, diabetes, and other metabolic disorders or comorbidities of obesity, in a subject by altering the subject's gut microbiota population, with the result of altering an energy balance in the subject. Generally speaking, to increase energy utilization/expenditure, decrease body fat, or promote weight loss, the relative abundance of microbiota within particular bacterial taxa can be altered. Altering microbiota can include changing a relative abundance of microbiota by increasing and/or decreasing the relative abundance of one or more microbiota.

The term "metabolic disorder" as used herein, refers to disorders, diseases, and conditions that are caused or characterized by abnormal weight gain, energy use or consumption, altered responses to ingested or endogenous nutrients, energy sources, hormones or other signaling molecules within the body or altered metabolism of carbohydrates, lipids, proteins, nucleic acids or a combination thereof. A metabolic disorder is associated with either a deficiency or excess in a metabolic pathway resulting in an imbalance in metabolism of nucleic acids, proteins, lipids, and/or carbohydrates. Factors affecting metabolism include, and are not limited to, the endocrine (hormonal) control system (e.g., the insulin pathway, the enteroendocrine hormones including GLP-1, PYY or the like), the neural control system (e.g., GLP-1 or other neurotransmitters or regulatory proteins in the brain) or the like. Some non-limiting examples can be obesity, diabetes, including type II diabetes, insulin-deficiency, insulin-resistance, insulin-resistance related disorders, glucose intolerance, syndrome X, inflammatory and immune disorders, osteoarthritis, dyslipidemia, metabolic syndrome, non-alcoholic fatty liver, abnormal lipid metabolism, cancer, neurodegenerative disorders, sleep apnea, hypertension, high cholesterol, atherogenic dyslipidemia, hyperlipidemic conditions such as atherosclerosis, hypercholesterolemia, and other coronary artery diseases in mammals, and other disorders of metabolism.

Disorders also included are conditions that occur or cluster together, and increase the risk for heart disease, stroke, diabetes, and obesity. Having just one of these conditions such as increased blood pressure, elevated insulin levels, excess body fat around the waist or abnormal cholesterol levels can increase the risk of the above mentioned diseases. In combination, the risk for coronary heart disease, stroke, insulin-resistance syndrome, and diabetes is even greater.

The increasing prevalence of obesity in the population has led to a parallel rise in surgical procedures, like bariatric surgery, as a treatment for obesity and related comorbid conditions. Surgical procedures can achieve a sustained weight reduction of up to 70% of excess body weight in the majority of patients, and are more effective than nonsurgical approaches. It has been discovered that gastric bypass can not only lead to early satiety, satiation, increased energy expenditure, improved glucose metabolism, and durable weight loss, but can also alter the microbiota in the gastrointestinal tract of the subject. Therefore, in an exemplary embodiment, a method of altering microbiota in a subject can be used to treat a weight related disorder, such as obesity.

The terms "treating," "treatment" or "intervention" refer to the administration or delivery of one or more therapeutic agents, compositions or procedures to a subject who has a condition or disorder or a predisposition toward a condition or disorder, with the purpose to prevent, alleviate, relieve, alter, remedy, ameliorate, improve, affect, slow or stop the progression, slow or stop the worsening of the disease, at least one symptom of condition or disorder, or the predisposition toward the condition or disorder.

The term "subject" as used herein refers to any living organism, including, but not limited to, humans, nonhuman primates such as chimpanzees and other apes and monkey species; farm animals such as cattle, sheep, pigs, goats and horses; domestic mammals such as dogs and cats; laboratory animals including rodents such as mice, rats, rabbits and guinea pigs, and the like. The term does not denote a particular age or sex. In a specific embodiment, the subject is human.

Microbiota

Methods and compositions are disclosed that include altering microbiota in a subject. As used herein, the term "microbiota" is used to refer to one or more bacterial communities that can be found or can exist (colonize) within a gastrointestinal tract of an organism. When referring to more than one microbiota, the microbiota may be of the same type (strain) or it may be a mixture of taxa, such as a mixture of Bacteroidetes, Firmicutes, Proteobacteria, Tenericutes, and Verrucomicrobia. In one aspect, methods and compositions are disclosed that alter the relative abundance of microbiota from phyla such as Bacteroidetes, Firmicutes, Tenericutes, Proteobacteria, and Verrucomicrobia or orders such as Bacteroidales, Erysipelotrichales, Clostridiales, Enterobacteriales and Verrucomicrobiales or genera such as *Alistipes, Clostridium, Escherichia, Allobaculum*, or *Akkermansia* in a gastrointestinal tract of a subject. The relative abundance microbiota can be altered by administering a pharmaceutical composition that includes microbiota from phyla such as Bacteroidetes, Proteobacteria, Firmicutes and Verrucomicrobia or orders such as Bacteroidales, Enterobacteriales, Clostridiales and Verrucomicrobiales or genera such as *Alistipes, Escherichia, Clostridium*, or *Akkermansia* or a compound that substantially increases the relative abundance of microbiota from phyla such as Bacteroidetes, Proteobacteria, Firmicutes, and Verrucomicrobia or orders such as Bacteroidales, Enterobacteriales, Clostridiales and Verrucomicrobiales or genera such as *Alistipes, Escherichia, Clostridium*, or *Akkermansia*, or substantially decreases the relative abundance of microbiota from phyla such as Firmicutes or Tenericutes or classes such as Mollicutes or orders such as Erysipelotrichales or genera such as *Allobaculum*.

In another aspect, methods and compositions are disclosed that selectively alter microbiota from phyla such as Bacteroidetes, Proteobacteria, Firmicutes, Tenericutes, and Verrucomicrobia or orders such as Bacteroidales, Enterobacteriales, Erysipelotrichales, Clostridiales, and Verrucomicrobiales or genera such as *Alistipes, Escherichia, Clostridium, Akkermansia* or *Allobaculum* in a gastrointestinal tract of an organism. Bacteroidetes, Firmicutes, Proteobacteria, Tenericutes, Verrucomicrobia, Bacteroidales, Enterobacteriales, Erysipelotrichales, Clostridiales, Verrucomicrobiales, *Alistipes, Escherichia, Clostridium, Akkermansia*, or *Allobaculum* can be selectively altered by administering a food or food supplement that includes Bacteroidetes, Firmicutes, Proteobacteria, Verrucomicrobia, Bacteroidales, Enterobacteriales, Clostridiales, Verrucomicrobiales, *Alistipes, Escherichia, Clostridium*, and/or *Akkermansia* or can substantially increase or decrease the relative abundance of Bacteroidetes, Firmicutes, Proteobacteria, Tenericutes, Verrucomicrobia, Bacteroidales, Enterobacteriales, Erysipelotrichales, Clostridiales, Verrucomicrobiales, *Alistipes, Escherichia, Clostridium, Akkermansia*, and/or *Allobaculum* in a gastrointestinal tract of an organism.

Additionally, the methods may include altering bacterial taxa, such as altering bacterial phyla, altering bacterial classes, bacterial orders, bacterial families, bacterial genera and/or bacterial species in a gastrointestinal tract of an organism. In particular, five bacterial phyla are disclosed, Bacteroidetes, Firmicutes, Proteobacteria, Tenericutes, and Verrucomicrobia. The methods and compositions include altering bacterial classes, bacterial orders, bacterial families, bacterial genera and/or bacterial species of one or more of the bacterial phyla Bacteroidetes, Firmicutes, Proteobacteria, Tenericutes, and Verrucomicrobia in a gastrointestinal tract of an organism. In an exemplary embodiment, the methods and compositions include altering bacterial classes, bacterial orders, bacterial families, bacterial genera and/or bacterial species of Bacteroidetes, Firmicutes, Proteobacteria, Tenericutes, or Verrucomicrobia in a gastrointestinal tract of an organism.

The phylum Verrucomicrobia is a newly described, divergent phylum within the Bacteria domain. Microbial communities of Verrucomicrobia have been isolated from yeast, soil, feces and fresh and marine waters. In addition, extremely acidophilic members have been discovered from hot springs that oxidize methane and use methane as a sole source of carbon and energy. Some species within Verrucomicrobia harbor genes homologous to those encoding eukaryotic tubulins. *Akkermansia*, found in the gastrointestinal tract and associated with gut health, can degrade mucin and host mucins as a sole source of carbon and nitrogen fuel. At present, six monophyletic subdivisions (subphyla, classes) are recognized within the phylum Verrucomicrobia on the basis of 16S rRNA gene library studies. In an exemplary embodiment, the composition can alter the relative abundance of bacteria from the class Verrucomicrobiae, bacteria from the order Verrucomicrobiales, bacteria from the family Verrucomicrobiaceae, and/or bacteria from the genus *Akkermansia*.

The phylum of Bacteroidetes contains three large classes of bacteria, Bacteroidia, Flavobacteria, and Sphingobacteria, that are distributed in the environment, including in soil, in sediments, seawater and in the guts and on the skin of animals. The predominantly Gram-negative bacteria are the most well-studied phylum since they are commonly found in the human intestine where they have a symbiotic host-bacterial relationship with humans. They assist in breaking down food and producing valuable nutrients and energy that the body needs. Bacteria from the genus *Alistipes* are generally bile acid resistant and may increase after a bile diversion-type surgery. In one embodiment, the composition can alter the relative abundance of bacteria from the class Bacteroidia, bacteria from the order Bacteroidales, bacteria from the family Rikenellaceae, and/or bacteria from the genus *Alistipes*.

Proteobacteria is the largest phylum of bacteria. As a group, these organisms show extreme metabolic diversity and represent the majority of known bacteria of medical, industrial, and agricultural significance. This is an evolutionarily, geologically, and environmentally important group. All Proteobacteria are Gram negative, with an outer membrane composed of lipopolysaccharides. Many have gas vesicles, flagella, or can move by gliding; they may have stalks, other appendages or the ability to form multicellular fruiting bodies. Most members are facultatively or obligately anaerobic, chemoautotrophs, and heterotrophic, but there are exceptions. Some species are able to carry out photosynthesis, others deposit sulphur within the cells or outside.

The Proteobacteria are divided into six sections, referred to as alpha through zeta, based on rRNA sequences. The alpha, beta, delta, and epsilon sections are monophyletic. Gammaproteobacteria is paraphyletic with respect to beta proteobacteria, i.e. Gammaproteobacteria consists of almost all the descendants of Betaproteobacteria. In one embodiment, the composition can alter the relative abundance of bacteria from the class Gammaproteobacteria, bacteria from the order Enterobacteriales, bacteria from the family Enterobacteriaceae, and/or bacteria from the genus *Escherichia*.

Tenericutes are a phylum of bacteria that lack a cell wall and do not contain muramic acid. This phylum includes the class, Mollicutes, that contains mycoplasms. Some are parasites of various animals and plants, living on or in the host's cells. Individual organisms are generally very small, typically only 0.2-0.3 μm in size and with a small genome size. They vary in form, although most have sterols that make the cell membrane somewhat more rigid. Many are able to move about through gliding or twisting. In one embodiment, the composition can alter the relative abundance of bacteria from the class Mollicutes, and/or bacteria from the genus *Allobaculum*.

Firmicutes are a phylum of bacteria that are mostly Gram positive. A few, however, have a porous pseudo-outer-membrane that causes them to stain Gram negative. Scientists once classified the Firmicutes to include all Gram-positive bacteria, but have recently defined them to be of a core group of related forms called the low –G+C. They are predominantly round cells, called cocci (singular coccus), or rod-like forms (bacillus). Many Firmicutes produce endospores, which are resistant to desiccation and can survive extreme conditions allowing them to live in various environments. The group is typically divided into Clostridia, which are anaerobes, and Bacilli, which are obligate or facultative anaerobes. The class Clostridia includes the family Lachnospiraceae, the family Ruminococcaceae, and the genus *Clostridium*. The class Bacilli includes the genus *Lactobacillus*. In one embodiment, the composition can alter the relative abundance of bacteria from the class Erysipelotrichi, bacteria from the order Erysipelotrichales, and/or bacteria from the family Erysipelotrichaceae.

In an exemplary embodiment, the microbiota disclosed can be a probiotic bacteria or non-pathogenic bacteria which, when the relative abundance altered, can confer a health benefit to the host. Probiotic strains generally have the ability to survive the passage through the upper part of the digestive tract when administered orally. They are nonpathogenic, non-toxic and exercise their beneficial effect on health on the one hand, possibly via ecological interactions with the resident flora in the digestive tract, and on the other hand, possibly via their ability to influence the immune and metabolic systems in a positive manner via the "GALT" (gut-associated lymphoid tissue). Depending on the definition of probiotics, these microbiota, when given in a sufficient number, have the ability to progress live through the intestine; however, they do not cross the intestinal barrier in large numbers and their primary effects are therefore induced in the lumen and/or the wall of the gastrointestinal tract. They then form part of the resident flora. This colonization (or transient colonization) allows the probiotic microbiota to exercise a beneficial effect, such as the repression of other micro-organisms present in the flora and interactions with the immune system of the intestine.

Relative Abundance of Microbiota

The methods include identifying at least one microbiota in a sample. Such a method for identifying a microbiota in a sample can include providing a sample comprising one or more microbiota, and detecting at least one microbiota in the sample. One embodiment of the method may include preparing a nucleic acid sample including a molecular indicator of identity from at least one microbiota present in the sample and detecting the molecular indicator of identity. For example, the method can involve preparing at least one nucleic acid sample by preparing a DNA sample. The molecular indicator of identity can be a polymorphic polynucleotide, such as an rRNA gene (for example, a 16S rRNA gene). The molecular indicator of identity can be detected by determining the nucleotide sequence of the polymorphic polynucleotide, such as the 16S rRNA gene, or a portion or subsequence thereof. Additional embodiments for detecting the molecular indicator of identity can also include PCR with selective primers, quantitative PCR with selective primers, DNA-DNA hybridization, RNA-DNA hybridization, in situ hybridization, and combinations thereof. For example, the polymorphic polynucleotide can be detected by hybridization to a specific probe. In such an example, the specific probe hybridizes to a polymorphic target nucleic acid, such as a 16S rRNA gene. Optionally, the nucleic acid can be hybridized to at least one array comprising a plurality of specific probes, e.g., a plurality of specific probes, each of which identifies a microbiota. Detecting the molecular indicator of identity can also be accomplished using protein probes (such as antibodies) that bind to polymorphic target proteins, for example polymorphic target proteins that identify the microbiota.

The method of altering microbiota can also include measuring the relative abundance of one or more microbiota in a sample from a subject. As used herein, the term "relative abundance" refers to the commonality or rarity of an organism relative to other organisms in a defined location or community. For example, the relative abundance can be determined by generally measuring the presence of a particular organism compared to the total presence of organisms in a sample.

The relative abundance of microbiota can be measured directly or indirectly. Direct measurements can include culture based methods. Indirect measurements can include comparing the prevalence of a molecular indicator of identity, such as ribosomal RNA (rRNA) gene sequences, specific for an organism or group of organisms in relation to the overall sample. For example, a ratio of rRNA specific for Bacteroidetes, Firmicutes, Proteobacteria, Tenericutes, or Verrucomicrobia in a total number of rRNA gene sequences obtained from a cecal sample can be used to determine the relative abundance of Bacteroidetes, Firmicutes, Proteobacteria, Tenericutes, or Verrucomicrobia in the cecal sample.

In one embodiment, the relative abundance of microbiota, such as Bacteroidetes, Firmicutes, Proteobacteria, Tenericutes, and Verrucomicrobia, within an individual subject may be calculated by measuring the ratio of one or more specific microbiota in a sample from an individual to obtain a microbiota profile of the subject. The relative abundance can be derived from the total abundance of microbiota present in a sample. As used herein, the "total abundance" refers generally to the total organisms in a sample. As used herein, "microbiota profile" refers to a representation, such as a graph, of the relative abundance of one or more microbiota in a subject or sample from a subject.

The relative abundance of microbiota can be measured by obtaining a sample from a subject. The sample can be saliva, feces, and stomach, intestinal and/or rectal content; tissue sample from a digestive tract tissue such as an oral tissue, esophagus, stomach, intestine, ileum, cecum, colon and/or rectum; an ascites within a gastrointestinal tissue; and any other sample that may be used by those familiar with assessing microbiota. In an exemplary embodiment, a relative abundance of gastrointestinal microbiota is measured.

The methods can also include measuring a relative abundance of microbiota in a biological sample, identifying one or more microbiota to produce a microbiota profile of microbiota found in a particular subject, e.g. individual having undergone a treatment or therapeutic intervention, or found in a particular location within the subject, e.g. gastrointestinal tract; and providing a composition comprising one or more substantially purified microbiota selected from the microbiota profile, such as a Bacteroidetes, Firmicutes, Proteobacteria, Tenericutes, and Verrucomicrobia. In certain embodiments, the methods can include identifying and categorizing microbiota in a subject. Typically, the identification is accomplished using culture-independent methods. For example, as disclosed herein, the microbiota can be identified by PCR using selective primers, quantitative PCR with selective primers, DNA-DNA hybridization, RNA-DNA hybridization and/or in situ hybridization. In some cases the hybridization is performed on a microarray. Additionally, PCR or high-throughput sequencing methods can detect over- and under-represented genes in the total bacterial population or transcriptomic or proteomic studies to identify lost or gained microbial transcripts or proteins within total bacterial populations. Alternatively, one or more species can be identified by determining the nucleotide sequence of a portion of a microbial genome, such as a 16S rRNA gene.

The methods can also include measuring total microbiota, individual microbiota taxa, such as phyla/classes/orders/families/genera/species, or measuring a combination of more than one microbiota taxa taken from a target location, or at a specific time before and/or after an activity, such as ingesting food or physical activity, or pre- or post-treatment, such as a therapeutic intervention like pharmaceutical therapy, gastric bypass, duodenojejunal bypass, biliopancreatic diversion, vertical sleeve gastrectomy, adjustable gastric banding, vertical banded gastroplasty, intragastric balloon therapy, gastric plication, Magenstrasse and Mill, small bowel transposition, biliary diversion, brown adipose tissue modulation (e.g., controlled activation, enhanced differentiation, supplemental implantation, etc.), pharmaceutical administration, electrical stimulation of nerves that innervate at least a portion of the gastrointestinal tract, therapies impacting circadian rhythms, bile acid modulation, intestinal mucus production and metabolism, and duodenal endoluminal barrier.

Individual relative abundances of microbiota may be obtained or total abundances of microbiota may be obtained over an extended time period. The abundances of microbiota can include one or more of any of the microbiota phyla/classes/orders/families/genera/species found in a gastrointestinal tract of an animal (e.g., a human), and can be performed by methods routinely used in the art including, by way of a non-limiting example, gastrointestinal tract content sampling. The relative abundance or total abundances of microbiota may also include measuring total microbiota present in a sample.

The relative abundance of one or more microbiota levels can also be determined before, during or after an activity. The activities may include, but are not limited to, physical activity, ingestion of food, and treatments, such as therapeutic interventions.

The relative abundance of one or more microbiota, a microbiota profile, can be compared to a target profile of relative abundances or total abundance of microbiota. The target profile can be a standardized microbiota profile obtained from one or more subjects of similar weight, age, gender, race, etc. The target profile can be a normalized microbiota profile from a healthy subject of similar weight, age, gender, race, etc. The target profile can be a microbiota profile from a healthy subject of similar weight, age, gender, race, etc that is responsive or demonstrates a favorable outcome to a treatment or therapeutic intervention. In a particular embodiment, the target profile is a microbiota profile from a healthy subject that is responsive to a therapeutic intervention, such as pharmaceutical therapy, gastric bypass, duodenojejunal bypass, biliopancreatic diversion, vertical sleeve gastrectomy, adjustable gastric banding, vertical banded gastroplasty, intragastric balloon therapy, gastric plication, Magenstrasse and Mill, small bowel transposition, biliary diversion, brown adipose tissue modulation (e.g., controlled activation, enhanced differentiation, supplemental implantation, etc.), pharmaceutical administration, electrical stimulation of nerves that innervate at least a portion of the gastrointestinal tract, therapies impacting circadian rhythms, bile acid modulation, intestinal mucus production and metabolism, duodenal endoluminal barrier, or similar manipulations of the gastrointestinal tract.

The term "target profile" is intended to encompass any standard or normal microbiota profile that can be useful as a benchmark against which "altered microbiota profiles" can be measured. One skilled in the art can select a reference target profile in a myriad of ways so long as statistically relevant measurements can be obtained. For example, a target profile, or target profile for microbiota can be selected as the average level exhibited by healthy young adults (e.g., aged 25 to 30 years old). Other standards or normal target profiles can be chosen depending upon the particular applications.

The relative abundance of one or more microbiota can be determined through repeated microbiota profiles taken before, concurrent with, and/or after a metabolic disorder treatment, such as administration of a composition or agent like a weight loss supplement, pharmaceutical therapy, brown adipose tissue modulation (e.g., controlled activation, enhanced differentiation, supplemental implantation, etc.), pharmaceutical administration, electrical stimulation of nerves that innervate at least a portion of the gastrointestinal tract, therapies impacting circadian rhythms, bile acid modulation, intestinal mucus production and metabolism, gastric bypass, duodenojejunal bypass, biliopancreatic diversion, vertical sleeve gastrectomy, adjustable gastric banding, vertical banded gastroplasty, intragastric balloon therapy, gastric plication, Magenstrasse and Mill, small bowel transposition, biliary diversion, duodenal endoluminal barrier, or similar manipulations of the gastrointestinal tract. The repeated microbiota profiles can be used to compare relative abundance of microbiota before, concurrent with, and/or after the treatment. Obtaining a microbiota profile after a treatment and comparing with pre-treatment profiles can also be used to determine or assess microbiota modifications that may be useful. The microbiota profile can be obtained at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 days or more prior to the treatment. The microbiota profile can also be performed at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 days or more after the treatment. The microbiota profile can be obtained concurrently with the treatment.

Not only can the relative abundance of microbiota be obtained, but measurements of one or more other molecules that may contribute to variations in relative abundance of microbiota, such as, but not limited to, microbiota metabolites, microbiota components, glucose concentrations, leptin levels, or insulin levels, may be obtained. The method of measuring other molecules that may contribute to relative abundance or total abundance of microbiota can include measuring the molecules in a sample from a subject. The sample can be the same sample used to obtain the relative abundance of microbiota, or it can be a different sample. The sample can be, for example, a fecal, a blood, a stomach content, and an intestinal content sample (e.g., luminal sample, mucus layer sample, mucosal adherent sample, etc.).

The methods and compositions may include altering the relative abundance of one or more microbiota, such as Bacteroidetes, Proteobacteria, Firmicutes, Tenericutes, and Verrucomicrobia phyla or Bacteroidales, Enterobacteriales, Erysipelotrichales, Clostridiales, and Verrucomicrobiales orders or *Alistipes, Escherichia, Clostridium, Allobaculum* and *Akkermansia* genera, at least about a one-fold increase or decrease. An exemplary embodiment may include a method for composition for altering the relative abundance of microbiota by administering substantially purified microbiota, such as Bacteroidetes, Proteobacteria, Firmicutes, and Verrucomicrobia, to a subject. For example, substantially purified Bacteroidales, Enterobacteriales, Erysipelotrichales, Clostridiales, Verrucomicrobiales, *Alistipes, Escherichia, Clostridium, Allobaculum*, or *Akkermansia* may be administered to a subject. The relative abundance of microbiota within an individual subject may be altered (e.g., increased) from at least about 1% to at least about 1000% or more depending on the desired result (e.g., increased energy utilization (weight loss)) and the individual subject. To treat a disorder, the relative abundance may be increased by at least about 5%, 10%, 20%, 30%, 40%, 50%, 60%, 70%, 80%, 90%, 100%, 150%, 200%, 250%, 300%, 350%, 400%, 450%, 500%, 600%, 700%, 800%, 900%, 1000%, 2000%, 5000% or more. In an exemplary embodiment, the relative abundance of Verrucomicrobia is increased by at least about 5%. In another embodiment, the relative abundance of at least one of Bacteroidetes, Proteobacteria, Firmicutes and Verrucomicrobia is increased by at least about 5%. In another embodiment, the relative abundance of at least one of Clostridia, Bacteroidales, Enterobacteriales, Clostridiales and Verrucomicrobiales is increased by at least about 5%. In another embodiment the relative abundance of at least one of Erysipelotichales and Tenericutes is decreased by at least about 5%.

Another aspect encompasses a combination therapy to regulate fat storage, energy utilization, and/or weight loss in a subject. In an exemplary embodiment, a combination for increasing energy utilization, decreasing body fat or for promoting weight loss may include combining the methods and compositions disclosed with a procedure or therapy such as a pharmaceutical therapy, gastric bypass, duodenojejunal bypass, biliopancreatic diversion, vertical sleeve gastrectomy, adjustable gastric banding, vertical banded gastroplasty, intragastric balloon therapy, gastric plication, Magenstrasse and Mill, small bowel transposition, biliary diversion, brown adipose tissue modulation (e.g., controlled activation, enhanced differentiation, supplemental implantation, etc.), pharmaceutical administration, electrical stimulation of nerves that innervate at least a portion of the gastrointestinal tract, therapies impacting circadian rhythms, bile acid modulation, intestinal mucus production and metabolism, duodenal endoluminal barrier or similar manipulations of the gastrointestinal tract. For example, a composition comprising a substantially purified microbiota, such as Bacteroidetes, Proteobacteria, Firmicutes, Verrucomicrobia, Bacteroidales, Enterobacteriales, Clostridiales, Verrucomicrobiales, *Alistipes, Escherichia, Clostridium*, or *Akkermansia* can be administered to the subject prior to, concurrently with or after a gastric bypass or other gastrointestinal or bariatric procedure.

Microbiota Compositions and Combination Compositions

Compositions are provided that can directly or indirectly alter the relative abundance of microbiota to a predetermined level, e.g. a therapeutic level, for a predetermined amount of time, e.g. until the next dose is administered. The predetermined level can be obtained from measured relative abundances of microbiota that result in a therapeutic response, e.g. weight loss.

In one aspect, compositions can alter the relative abundance of microbiota directly, such as through administration of microbiota in a pharmaceutical composition or a food, drink, dietary supplement, and/or food additive to be consumed by a subject. The compositions may include microbiota that are whole bacteria. Microbiota may also be viable (live), dormant, inactivated or dead bacteria. In an exemplary embodiment, the composition includes a live bacterial strain of microbiota from phyla such as Bacteroidetes, Proteobacteria, Firmicutes and Verrucomicrobia or orders such as Bacteroidales, Enterobacteriales, Clostridiales and Verrucomicrobiales or genera such as *Alistipes, Escherichia, Clostridium*, and *Akkermansia*.

The composition can also include mixtures of bacterial strains. The mixtures may include microbiota that are viable (live), dormant, inactivated or dead, or any combination thereof. In some embodiments, the microbiota can include a mixture or combination of live bacterial strains.

A combination of bacteria from different phyla, such as Bacteroidetes, Firmicutes, Proteobacteria, Tenericutes, and Verrucomicrobia, can also exhibit a synergistic effect in certain applications (i.e. an effect which is greater than the additive effect of the bacteria when used separately). In addition, a combination of bacteria from different phyla, different classes, different orders and different families can be useful. For example, combinations which, in addition to having an effect on the mammal as single components, may influence other microbiota, e.g. by producing metabolites which are used as an energy source by other microbiota, or maintaining physiological conditions which favor or disfavor other microbiota. In one embodiment, the composition includes a mixture of at least two or more bacterial strains.

When the composition includes a combination of one or more microbiota, the microbiota can be from the same or different phyla/classes/orders/families/genera/species. In an exemplary embodiment, the composition includes at least one microbiota from phyla such as Bacteroidetes, Proteobacteria, Firmicutes and Verrucomicrobia or orders such as Bacteroidales, Enterobacteriales, Clostridiales and Verrucomicrobiales or genera such as *Alistipes, Escherichia, Clostridium*, and *Akkermansia*. In another embodiment, the composition includes Verrucomicrobia, such as Verrucomicrobiales. In another embodiment, the composition includes Verrucomicrobia, such as *Akkermansia*. In yet another embodiment, the composition includes Verrucomicrobia and at least one or more of Bacteroidetes, Firmicutes and Proteobacteria. In another embodiment, the composition includes Bacteroidetes, such as Bacteroidales. For example, the composition can include *Alistipes*. In another embodiment, the composition includes Enterobacteriales, such as *Escherichia*. In another embodiment, the composition can include Firmicutes, such as *Clostridium*.

In an exemplary embodiment, the composition can include bacteria from the class Verrucomicrobiae, bacteria from the order Verrucomicrobiales, bacteria from the family Verrucomicrobiaceae, and/or bacteria from the genus *Akkermansia*. In another embodiment, the composition can additionally include bacteria from at least one or more of Bacteroidetes, Firmicutes, and Proteobacteria. In another embodiment, the composition can include bacteria from the class Gammaproteobacteria, bacteria from the order Enterobacteriales, bacteria from the family Enterobacteriaceae, and/or bacteria from the genus *Escherichia*. In yet another embodiment, the composition can include bacteria from the class Bacteroidia, bacteria from the order Bacteroidales, bacteria from the family Rikenellaceae, and/or bacteria from the genus *Alistipes*. In another embodiment, the composition can include bacteria from the class Clostridia, bacteria from the order Lachnospiraceae, bacteria from the family Ruminococcaceae, and/or bacteria from the genus *Clostridium*.

In another exemplary embodiment, the composition can include bacteria from the class Bacteroidia, bacteria from the order Bacteroidales, bacteria from the family Rikenellaceae, and/or bacteria from the genus *Alistipes*. In another embodiment, the composition can additionally include bacteria from at least one or more of Verrucomicrobia, Firmicutes, and Proteobacteria. In another embodiment, the composition can include bacteria from the class Gammaproteobacteria, bacteria from the order Enterobacteriales, and/or bacteria from the family Enterobacteriaceae. In yet another embodiment, the composition can include bacteria from the class Verrucomicrobiae, bacteria from the order Verrucomicrobiales, and/or bacteria from the family Verrucomicrobiaceae. In another embodiment, the composition can include bacteria from the class Clostridia, bacteria from the order Lachnospiraceae, bacteria from the family Ruminococcaceae, and/or bacteria from the genus *Clostridium*.

In yet another embodiment, the composition can include bacteria from the class Clostridia, bacteria from the order Clostridiales, bacteria from the family Lachnospiraceae, bacteria from the family Ruminococcaceae, and/or bacteria from the genus *Clostridium*. In another embodiment, the composition can additionally include bacteria from at least one or more of Verrucomicrobia, Bacteroidetes, and Proteobacteria. In another embodiment, the composition can include bacteria from the class Gammaproteobacteria, bacteria from the order Enterobacteriales, and/or bacteria from the family Enterobacteriaceae. In yet another embodiment, the composition can include bacteria from the class Verrucomicrobiae, bacteria from the order Verrucomicrobiales, and/or bacteria from the family Verrucomicrobiaceae. In yet another embodiment, the composition can include bacteria from the class Bacteroidia, bacteria from the order Bacteroidales, and/or bacteria from the family Rikenellaceae.

In another embodiment, the composition can include bacteria from two or more phyla. For example, the composition can include bacteria from the phylum Bacteroidetes and bacteria from the phylum Verrucomicrobia. In another embodiment, the composition can include bacteria from two or more classes. For example, the composition can include bacteria from the class Clostridia and bacteria from the class Bacteroidia. In another example, the composition can include bacteria from the class Clostridia and bacteria from the class Verrucomicrobiae. In another example, the composition can include bacteria from two or more orders. For example, the composition can include bacteria from the order Bacteroidales and bacteria from the order Enterobacteriales. In another example, the composition can include bacteria from the order Verrucomicrobiales and bacteria from the order Enterobacteriales. In another embodiment, the composition can include bacteria from two or more genera. For example, the composition can include two or more of *Alistipes, Escherichia, Clostridium*, and *Akkermansia*.

The microbiota can also be substantially purified. The term "substantially purified" as used herein refers to a bacterial strain or a mixture of more than one bacterial strains (e.g., Bacteroidetes, Firmicutes, Proteobacteria, or Verrucomicrobia) that are substantially enriched in a sample. The sample can be substantially purified or enriched for the bacterial strain or mixture of strains of interest such that the sample is at least about 50%, 60%, 70%, 80%, 85%, 90%, 95%, 99% or greater of the desired bacterial strain(s) or less than about 40%, 30%, 20%, 15%, 14%, 13%, 12%, 11%, 10%, 9%, 8%, 7%, 6%, 5%, 4%, 3%, 2%, 1% or less of the undesirable or other bacterial strains present. In an exemplary embodiment, a composition includes substantially purified Verrucomicrobia. For example, the composition includes a substantially purified *Akkermansia*. In another embodiment, a composition includes substantially purified Enterobacteriales. For example, the composition includes a substantially purified *Escherichia*. In another embodiment, a composition includes substantially purified Bacteroidales. For example, the composition includes a substantially purified *Alistipes*. In another embodiment, a composition includes a substantially purified Clostridia. For example, the composition includes a substantially purified *Clostridium*. In another exemplary embodiment, the composition includes substantially purified Verrucomicrobia and at least one or more of substantially purified Bacteroidetes, Firmicutes and Proteobacteria. Another embodiment is directed to a pharmaceutical composition for altering microbiota including a therapeutically effective amount of substantially purified microbiota, such as Verrucomicrobia, Bacteroidales, Clostridiales, Enterobacteriales, *Alistipes, Escherichia, Clostridium*, and/or *Akkermansia*.

Methods and compositions can also include treating weight related disorders, such as obesity, by substantially altering a relative abundance of microbiota, by increasing or decreasing microbiota from phyla such as Bacteroidetes, Proteobacteria, Firmicutes, Tenericutes and Verrucomicrobia or classes such as Mollicutes or orders such as Bacteroidales, Enterobacteriales, Erysipelotrichales, Clostridiales and Verrucomicrobiales or genera such as *Alistipes, Escherichia, Clostridium, Allobaculum* and *Akkermansia*, in a gastrointestinal tract of a subject without or in addition to a surgical procedure. In one embodiment, the methods and compositions can include increasing a relative abundance of Verrucomicrobia and/or Enterobacteriales. The methods and compositions can further include increasing a relative abundance of Bacteroidetes. In another embodiment, the methods and compositions can include increasing a relative abundance of Verrucomicrobia, Bacteroidetes, Firmicutes, and/or Proteobacteria. In an exemplary embodiment, the methods and compositions can further include increasing a relative abundance of Bacteroidales, Enterobacteriales, Clostridia, Clostridiales, Verrucomicrobiae, Verrucomicrobiales, *Alistipes, Escherichia, Clostridium*, and/or *Akkermansia*. In another embodiment, methods and compositions can increase a relative abundance of Enterobacteriales. In another embodiment, methods and compositions can increase a relative abundance of *Escherichia*. In another embodiment, methods and compositions can increase a relative abundance of *Alistipes*. In another embodiment, methods and compositions can increase a relative abundance of *Clostridium*. In another embodiment, methods and compositions can increase a relative abundance of *Akkermansia*. In yet another embodiment, the methods and compositions can include decreasing a relative abundance of Firmicutes and/or Tenericutes. In another embodiment, methods and compositions can decrease a relative abundance of Erysipelotrichales. In another embodiment, methods and compositions can decrease a relative abundance of Mollicutes. In another embodiment, methods and compositions can decrease a relative abundance of *Allobaculum*.

Methods and compositions of altering a relative abundance of microbiota can result in altered metabolic function. For example, altering metabolic function can include increasing energy expenditure and/or increasing glucose metabolism. Energy expenditure can be increased by at least about 5%, 6%, 7%, 8%, 9%, 10%, 15%, or 20%. The relative abundance of microbiota can be altered such that at least one bacterial taxa has an LDA of at least 2. In one embodiment, a relative abundance of microbiota can be altered by increasing the relative abundance of propionate-producing bacteria in a gastrointestinal tract of a subject. For example, the relative abundance of *E. coli* can be increased. Propionate-producing bacteria can be increased such that the level of propionate in the gastrointestinal tract is increased by at least about 50%, 60%, 70%, 80%, 90%, 99%, 100%, or %150%. In another embodiment, a relative abundance of microbiota can be altered to reduce acetate in a gastrointestinal tract of a subject. In another embodiment, a ratio of short chain fatty acids can be altered in a gastrointestinal tract of a subject. For example, the ratio can be altered by manipulating bacteria in a gastrointestinal tract of a subject. Alternatively, the ratio can be altered by creating bacteria to alter a ratio of short chain fatty acids in an environment. In another example, a cocktail of short chain fatty acids can be administered to a subject.

Another aspect includes compositions including compounds or agents that alter the relative abundance of microbiota indirectly, such as through the administration of compound(s) or agent(s) that affect the growth, survival, persistence, transit or existence of one or more specific microbiota, such as Bacteroidetes, Firmicutes, Proteobacteria, Tenericutes and Verrucomicrobia. In one embodiment, the composition can increase a relative abundance of bacteria. For example, the composition can increase a relative abundance of bacteria from the class Bacteroidia, Gammaproteobacteria, Clostridia, and/or Verrucomicrobiae or bacteria from the order Bacteroidales, Enterobacteriales, Lachnospiraceae, and/or Verrucomicrobiales or bacteria from the family Rikenellaceae, Enterobacteriaceae, Clostridiaceae, and/or Verrucomicrobiaceae or bacteria from the genus *Alistipes, Escherichia, Clostridium*, and/or *Akkermansia*. In one embodiment, the composition can decrease a relative abundance of bacteria. For example, in one embodiment, the composition can decrease the relative abundance of bacteria from the class Erysipelotrichi, bacteria from the order Erysipelotrichales, and/or bacteria from the family Erysipelotrichaceae. In another example, the composition can decrease the relative abundance of bacteria from the class Mollicutes and/or bacteria from the genus *Allobaculum*.

The compounds or agents can be antibiotic treatments and/or antibacterial agents. Antibiotics can also include naturally occurring antibacterial agents (e.g., magainins, defensins and others) or specialized nutrient mixtures that alter the relative composition of the microbiota. The compounds or agents can also be prebiotics. The term "prebiotic" refers to a component which increases the number of probiotic bacteria in the intestine. Thus, prebiotics as used herein may refer to any non-viable component that is specific to a bacteria thought to be of positive value, e.g. Verrucomicrobia. The administration of one or more prebiotic compounds may selectively enhance the relative abundance or general growth of one or more specific microbiota in vivo resulting in a pronounced health benefit, such as weight loss. Some nonlimiting examples of prebiotics can include bacterial cell wall components such as peptidoglycans, bacterial nucleic acids such as DNA and RNA, bacterial membrane components, and bacterial structural components such as proteins, carbohydrates, lipids and combinations of these such as lipoproteins, glycolipids and glycoproteins. Additional examples can also include organic acids, inorganic acids, bases, proteins and peptides, enzymes and co-enzymes, amino acids and nucleic acids, carbohydrates, lipids, glycoproteins, lipoproteins, glycolipids, vitamins, bioactive compounds, metabolites containing an inorganic component, small molecules, for example nitrous molecules or molecules containing a sulphurous acid, resistant starch, potato starch or high amylose starch, modified starches (including carboxylated starches, acetylated, propionated, and butyrated starches), non-digestible oligosaccharides such as fructooligosaccharides, glucooligosaccharides, xylooligosaccharides, galactooligosaccharides, arabinoxylans, arabinogalactans, galactomannans, polydextrose, oligofructose, inulin, derivatives of these, but not excluding other oligosaccharides able to exert prebiotic effects, other soluble fibers, and combinations thereof.

The compounds or agents can also be provided in a food, drink, dietary supplement, and/or food additive or can be used to modify a food, drink, dietary supplement, and/or food additive.

Yet another aspect can be directed to compositions that include combinations of components that alter the relative abundance of microbiota directly and indirectly. In one embodiment, a combined administration of microbiota with one or more compounds or agents, such as prebiotics that foster the growth, survival, persistence, transit or existence of one or more specific microbiota, otherwise termed as 'synbiotic'. The combination may result in a more pronounced health benefit, such as greater weight loss or faster weight loss.

The composition can be combinations of one or more microbiota, such as at least one microbiota from phyla such as Bacteroidetes, Proteobacteria, Firmicutes, and Verrucomicrobia or orders such as Bacteroidales, Enterobacteriales, Clostridiales, and Verrucomicrobiales or genera such as *Alistipes, Clostridium, Escherichia* and *Akkermansia*, and one or more compounds or agents that foster the growth, survival, persistence, transit or existence of microbiota. The compounds or agents can be antibiotic treatments and/or antibacterial agents, e.g., 25-50 mg/kg/day for penicillin, 40-60 mg/kg/day for vancomycin, and 25-50 mg/kg/day for tetracycline (see, e.g., Nelson's Pocket Book of Pediatric Antimicrobial Therapy, 2002-2003, 15.sup.th Ed. J. Bradley & J. Nelson, eds., Lippincott Williams and Wilkins), prebiotics including bacterial components such as bacterial cell wall components such as peptidoglycan, bacterial nucleic acids such as DNA and RNA, bacterial membrane components, and bacterial structural components such as proteins, carbohydrates, lipids and combinations of these such as lipoproteins, glycolipids and glycoproteins, bacterial metabolites, organic acids, inorganic acids, bases, proteins and peptides, enzymes and co-enzymes, amino acids and nucleic acids, carbohydrates, lipids, glycoproteins, lipoproteins, glycolipids, vitamins, bioactive compounds, metabolites containing an inorganic component, and small molecules such as nitrous molecules or molecules containing a sulphurous acid, resistant starch, potato starch or high amylose starch, modified starches (including carboxylated starches, acetylated, propionated, and butyrated starches), non-digestible oligosaccharides such as fructooligosaccharides, glucooligosaccharides, xylooligosaccharides, galactooligosaccharides, arabinoxylans, arabinogalactans, galactomannans, polydextrose, oligofructose, inulin, derivatives of these, but not excluding other oligosaccharides able to exert prebiotic effects, other soluble fibers, and combinations thereof.

The above compositions can also include, for example, amino acids, amino sugars, sugar alcohols, proteins, saccharides, di-saccharides, oligo-saccharides, poly-saccharides, nucleic acids, buffers, surfactants, lipids, liposomes, other excipients, and mixtures thereof. Other useful components can include steroids, anti-inflammatory agents, non-steroidal anti-inflammatory agents, analgesics, cells, anti-inflammatory agents, growth factors, growth factor fragments, small-molecule wound healing stimulants, hormones, cytokines, peptides, antibodies, enzymes, isolated cells, platelets, immunosuppressants, nucleic acids, cell types, viruses, virus particles, essential nutrients, minerals, metals, or vitamins, and combinations thereof. Additionally, the composition can include a diluent, such as water, saline, or a buffer.

Screening for Compounds or Agents that Alter Microbiota

As disclosed above, a variety of compounds or agents can be useful for altering microbiota in a subject. Such compounds or agents can include but are not limited to antibiotic treatments and/or antibacterial agents, prebiotics such as bacterial cell wall components, bacterial nucleic acids such as DNA and RNA, bacterial membrane components, and bacterial structural components such as proteins, carbohydrates, lipids and combinations of these such as lipoproteins, glycolipids and glycoproteins, organic acids, inorganic acids, bases, proteins and peptides, enzymes and co-enzymes, amino acids and nucleic acids, carbohydrates, lipids, glycoproteins, lipoproteins, glycolipids, vitamins, bioactive compounds, metabolites containing an inorganic component, small molecules, for example nitrous molecules or molecules containing a sulphurous acid, resistant starch, potato starch or high amylose starch, modified starches (including carboxylated starches, acetylated, propionated, and butyrated starches), non-digestible oligosaccharides such as fructooligosaccharides, glucooligosaccharides, xylooligosaccharides, galactooligosaccharides, arabinoxylans, arabinogalactans, galactomannans, polydextrose, oligofructose, inulin, derivatives of these, but not excluding other oligosaccharides able to exert prebiotic effects, other soluble fibers, and combinations thereof.

The methods provided herein also can include methods of screening for and testing compounds' or agents' ability to alter the relative abundance of select microbiota in a subject. Some of the methods provided herein are screening methods for testing the ability of a pharmaceutical composition to alter microbiota from phyla such as Bacteroidetes, Proteobacteria, Firmicutes, Tenericutes, and Verrucomicrobia or orders such as Bacteroidales, Enterobacteriales, Erysipelotrichales, Clostridiales and Verrucomicrobiales or genera such as *Alistipes, Escherichia, Clostridium, Allobaculum* and *Akkermansia*. Other methods provided herein also can include testing compounds or agents in a food, drink, dietary supplement, and/or food additive for the ability to alter microbiota. Such methods thereby identify a pharmaceutical composition or a food, drink, dietary supplement, and/or food additive that is capable of increasing or decreasing the relative abundance of one or more microbiota from phyla such as Bacteroidetes, Proteobacteria, Firmicutes, Tenericutes, and Verrucomicrobia or orders such as Bacteroidales, Enterobacteriales, Erysipelotrichales, Clostridiales and Verrucomicrobiales or genera such as *Alistipes, Escherichia, Clostridium, Allobaculum* and *Akkermansia*.

Any of a variety of diagnostic factors can be monitored as indicators of efficacy, such as those known in the art. For example, weight changes, blood pressure, serum insulin/glucose levels, energy expenditure, breathing, color, temperature or other diagnostic indicators that can be measured to determine efficacy of the compound or agent. In addition, the presence or absence or level of one or more components in a sample from a subject can also be factors for determining efficacy of the compound or agent. Typical samples can include blood and urine samples, where the presence or absence or level of one or more components can be determined by performing, for example, a blood panel or a urine panel diagnostic test. Exemplary components indicative of a subject's health include, but are not limited to, white blood cell count, hematocrit, and protein concentration. In an exemplary embodiment, monitoring weight loss or alleviation of a disorder is used as an indicator of efficacy of the compound or agent as a pharmaceutical or food, drink, dietary supplement, and/or food additive.

The methods can also include monitoring the relative abundance of microbiota in a biological sample. For example, as disclosed herein, the microbiota can be monitored by PCR using selective primers, quantitative PCR with selective primers, DNA-DNA hybridization, RNA-DNA hybridization and/or in situ hybridization. Additionally, PCR or high-throughput sequencing methods can detect over- and under-represented genes in the total bacterial population or transcriptomic or proteomic studies to identify lost or gained microbial transcripts or proteins within total bacterial populations to monitor changes in relative abundance of specific microbiota from phyla such as Bacteroidetes, Proteobacteria, Firmicutes, Tenericutes, and Verrucomicrobia or orders such as Bacteroidales, Enterobacteriales, Erysipelotrichales, Clostridiales and Verrucomicrobiales or genera such as *Alistipes, Escherichia, Clostridium, Allobaculum* and *Akkermansia*. Alternatively, the relative abundance of one or more microbiota can be monitored by measuring the relative abundance of specific microbial genomes, such as a 16S rRNA gene, within total bacterial populations.

Provided herein is a kit for monitoring efficacy of an administered therapy as measured by changes in select microbiota. The kit can test a sample from a subject for the relative abundance of one or more microbiota from phyla such as Bacteroidetes, Proteobacteria, Firmicutes, Tenericutes, and Verrucomicrobia or orders such as Bacteroidales, Enterobacteriales, Erysipelotrichales, Clostridiales and Verrucomicrobiales or genera such as *Alistipes, Escherichia, Clostridium, Allobaculum* and *Akkermansia*. In some embodiments, the kit can contain reagents, devices, or components for detecting the relative abundance of microbiota from phyla such as Bacteroidetes, Proteobacteria, Firmicutes, Tenericutes, and Verrucomicrobia or orders such as Bacteroidales, Enterobacteriales, Erysipelotrichales, Clostridiales and Verrucomicrobiales or genera such as *Alistipes, Escherichia, Clostridium, Allobaculum* and *Akkermansia* and a control. Exemplary kits can include reagents, devices, or components to measure indicators of efficacy as provided herein and can, optionally, include one or more components such as instructions for use, devices, or components for detecting the selected microbiota or the relative abundance of the selected microbiota in a sample and, optionally, a device for obtaining and/or processing a sample from a subject. In one embodiment, the kit can include primers that selectively hybridize to nucleic acids from Verrucomicrobiales, Bacteroidales, Clostridiales, Erysipelotrichales, or Enterobacteriales species and hybridization reagents.

Formulations

The disclosed compositions can be formulated as a pharmaceutical composition. Such pharmaceutical compositions can include a pharmaceutically acceptable carrier. An exemplary embodiment is directed to a pharmaceutical composition for altering microbiota including a therapeutically effective amount of substantially microbiota from phyla such as Bacteroidetes, Proteobacteria, Firmicutes, Tenericutes, and Verrucomicrobia or orders such as Bacteroidales, Enterobacteriales, Erysipelotrichales, Clostridiales and Verrucomicrobiales or genera such as *Alistipes, Escherichia, Clostridium, Allobaculum* and/or *Akkermansia*, and pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. In one embodiment, formulations and compositions of the present invention can be incorporated into pharmaceutical compositions suitable for delivery to a subject. A pharmaceutical composition may also comprise a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition.

The compositions can be formulated in a variety of forms. These include, for example, liquid, semi-solid and solid dosage forms, such as liquid solutions (e.g., injectable and infusible solutions), dispersions or suspensions, tablets, pills, powders, liposomes, suppositories, and other formulations. The compositions can also be formulated for high drug concentrations. The compositions can further be sterile and stable under the conditions of manufacture and storage. Sterile injectable solutions can be prepared by incorporating the compositions in a required amount of an appropriate solvent with one or a combination of ingredients enumerated above, as required, followed by filtered sterilization.

Exemplary forms of the compositions can depend on the intended mode of delivery and therapeutic application. In one embodiment, the composition is formulated for oral delivery. Some compositions can be in the form of pill-based delivery, such as disclosed in U.S. patent application Ser. No. 12/976,648 entitled "Pill Catcher," filed Dec. 22, 2010, and delayed release methods. In one embodiment, the pill-based delivery can be part of the system that allows the delivery to occur at a precise location within the gastrointestinal tract. In another embodiment, the compositions can be formulated in a delayed release formulation. In another embodiment, the composition can be encapsulated in a coating that does not begin to degrade until it exits the exits the stomach of a patient. In another embodiment, the composition can be prepared with a carrier that will protect the composition against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978. "Sustained release" refers to release of a composition or an active compound thereof over a prolonged period of time relative to that achieved by delivery of a conventional formulation of the composition.

Another type of composition includes activatable forms, such as formulating a composition with microbiota in a dormant or inactive state, such as, a lyophilized state. In combination compositions, the microbiota may be in a dormant or inactive state or the compounds or agents that foster microbiota can be inactive. In an exemplary embodiment, the composition is formulated to include at least one of a dormant or inactive microbiota and inactive compounds or agents that foster microbiota.

The disclosed compositions and combination compositions can also be formulated as a food, drink, dietary supplement, and/or additive. Such compositions are those that are suitable for human and/or animal consumption. A skilled person will be readily aware of specific formulations of the microbiota which can be used in oral or ingestible formulations and are considered suitable for human and/or animal administration. Many compositions are used for the manufacture of food or food additive/supplemental; consequently a further important aspect is the provision of a human or animal food or food additive/supplemental including microbiota from phyla such as Bacteroidetes, Proteobacteria, Firmicutes and Verrucomicrobia or orders such as Bacteroidales, Enterobacteriales, Clostridiales, and Verrucomicrobiales or genera such as *Alistipes, Escherichia, Clostridium*, and *Akkermansia*, to increase weight loss in a mammal.

Consumable compositions can be formulated to include a sweetener(s), a stabilizer(s) or binder(s), a humectant(s), and/or natural and/or artificial flavors. The compositions may also include natural and/or artificial colors and preservatives. In one implementation, the compositions may include monosaccharides, di-saccharides and poly-saccharides such as but not limited to, sucrose (sugar), dextrose, maltose, dextrin, xylose, ribose, glucose, mannose, galactose, sucromalt, fructose (levulose), invert sugar, corn syrups, maltodextrins, fructo oligo saccharide syrups, partially hydrolyzed starch, corn syrup solids, polydextrose, soluble fibers, insoluble fibers, natural cane juice, gelatin, citric acid, lactic acid, natural colors, natural flavors, fractionated coconut oil, carnauba wax, or combinations thereof.

Dosage

The microbiota compositions can also include a "therapeutically effective amount," or an "effective amount." A "therapeutically effective amount" refers to an amount effective, at dosages and for periods of time necessary, to achieve the desired therapeutic result. A therapeutically effective amount of a composition may vary according to factors such as the disease state, age, sex, and weight of the individual, and the ability of the composition to elicit a desired response in the individual. A therapeutically effective amount is also one in which any toxic or detrimental effects of the composition are outweighed by the therapeutically beneficial effects. In an exemplary embodiment, a therapeutically effective amount of the microbiota composition is one in which the amount increases a relative abundance of one or more microbiota. For example, the therapeutically effective amount of Verrucomicrobia increases a relative abundance of Verrucomicrobia in a subject.

The dosage of the compositions can be dependent on the types of microbiota present in the composition. The dosage can also be determined based on a relative abundance of one or more microbiota present in the subject. The dosage can also be determined by additional treatments or therapeutic interventions, such as procedures like administration of a composition or agent like a weight loss supplement, pharmaceutical therapy, brown adipose tissue modulation (e.g., controlled activation, enhanced differentiation, supplemental implantation, etc.), pharmaceutical administration, electrical stimulation of nerves that innervate at least a portion of the gastrointestinal tract, therapies impacting circadian rhythms, bile acid modulation, intestinal mucus production and metabolism, gastric bypass, duodenojejunal bypass, biliopancreatic diversion, vertical sleeve gastrectomy, adjustable gastric banding, vertical banded gastroplasty, intragastric balloon therapy, gastric plication, Magenstrasse and Mill, small bowel transposition, biliary diversion, duodenal endoluminal barrier, or similar manipulations of the gastrointestinal tract.

In one embodiment, the composition can be effective to alter the relative abundance of one or more microbiota. In another embodiment, the composition can be effective to increase a relative abundance of the microbiota in a subject. In one embodiment, the composition can increase or decrease a relative abundance of a specific strain of microbiota from phyla such as Bacteroidetes, Proteobacteria, Firmicutes, Tenericutes, and Verrucomicrobia or orders such as Bacteroidales, Enterobacteriales, Erysipelotrichales, Clostridiales and Verrucomicrobiales or genera such as *Alistipes, Escherichia, Clostridium, Allobaculum*, and *Akkermansia*, in a subject. In an exemplary embodiment, the composition can increase a relative abundance of microbiota from phyla such as Bacteroidetes, Proteobacteria, Firmicutes, and Verrucomicrobia or orders such as Bacteroidales, Verrucomicrobiales, Clostridiales and Enterobacteriales or genera such as *Alistipes, Escherichia, Clostridium*, and *Akkermansia* in a subject.

In another embodiment, the composition can also be effective to alter microbiota in the subject so that after administration of the composition the microbiota in the subject mimics a microbiota found in a subject responsive to a gastric bypass or other gastrointestinal or bariatric procedure. The composition can be effective to alter microbiota to mimic microbiota from normal, healthy subjects of similar weight, age, gender, race, etc. In an exemplary embodiment, the microbiota can be altered, increased or decreased, to mimic one or more subjects of similar weight, age, gender, race, etc that are responsive or demonstrate a favorable outcome to a surgical procedure or therapeutic intervention, such as gastric bypass or other gastrointestinal bariatric or metabolic procedure, for the treatment of obesity, diabetes, other metabolic disorders or comorbidities of obesity. In an exemplary embodiment, the composition can be effective to alter microbiota in the subject to mimic microbiota found in a subject, such as a subject that is responsive to a surgical procedure like gastric bypass or other gastrointestinal bariatric or metabolic procedures.

Dosage regimens may be adjusted to provide the optimum desired response (e.g., a therapeutic or prophylactic response). For example, a single bolus may be delivered, several divided doses may be delivered over time or the dose may be proportionally reduced or increased as indicated by the exigencies of the therapeutic situation. It is especially advantageous to formulate parenteral compositions in dosage unit form for ease of delivery and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of individuals.

An exemplary dosage of a composition when employed in the method provided can be in the range from about 0.001 to about 100 mg/kg body weight per day, from about 0.01 to about 50 mg/kg body weight per day, such as from about 0.05 to about 10 mg/kg body weight per day, delivered in one or most doses, such as from 1 to 3 doses. In an exemplary embodiment, the composition includes substantially purified Verrucomicrobia or one or more of substantially purified Verrucomicrobia, Bacteroidetes, Firmicutes and Proteobacteria in the range of about 0.01 to about 50 mg/kg body weight per day, delivered in one to three doses. The exact dosage will depend upon the frequency and mode of delivery, the gender, age, weight and general condition of the subject treated, the nature and severity of the condition treated, any concomitant diseases to be treated and other factors evident to those skilled in the art.

In one embodiment, composition includes substantially purified microbiota, such as Verrucomicrobia, Bacteroidetes, Firmicutes and/or Proteobacteria, at a total concentration in the range of about 0.001 mg/kg to about 100 mg/kg. In another embodiment, the composition includes substantially purified microbiota, such as Verrucomicrobia, Bacteroidetes, Firmicutes and/or Proteobacteria, at a total concentration in the range of about 0.1 mg/kg to about 50 mg/kg. In yet another embodiment, the composition includes substantially purified microbiota, such as Verrucomicrobia, Bacteroidetes, Firmicutes and/or Proteobacteria, at a total concentration in the range of about 1 mg/kg to about 10 mg/kg.

Delivery

The microbiota composition can be delivered or administered by a variety of methods known in the art. The terms "delivery," "deliver," "administration" and "administer" are used interchangeable herein. As will be appreciated by the skilled artisan, the route and/or mode of delivery will vary depending upon the desired results. In one embodiment, the microbiota composition is delivered perorally. In another embodiment, the microbiota composition is delivered orally. Yet another mode of delivery can include methods and combinations for delivery to the gut.

The microbiota composition can be delivered to target regions and/or structures within the subject. Regions that can be targeted within the gastrointestinal tract can include, but are not limited to, the stomach, biliopancreatic limb, Roux limb, common limb, ileum, cecum, or colon. Structures can be targeted that constitute differentiated ecological niches with specific pH range, temperature, moisture, and metabolite content. Diseases and conditions associated with altered microbial profiles may exhibit either the presence of a novel microbe(s), absence of a normal microbe(s), or an alteration in the proportion of microbes.

Delivery of the microbiota composition can be targeted to one or more regions in a subject. The regions can include but are not limited to a region within the gastrointestinal tract. In an exemplary embodiment, the delivery is targeted to an oral cavity, stomach, biliopancreatic limb, Roux limb, common limb, small intestine, ileum, cecum, large intestine, or colon of a gastrointestinal tract. The delivery can also be targeted to one or more tissues in a subject. The tissues can include any tissue in a gastrointestinal tract, such as a stomach, biliopancreatic limb, Roux limb, common limb, small intestine, ileum, cecum, large intestine, or colon.

The composition can be delivered before, current with or after a therapeutic treatment, such as procedures like administration of a composition or agent like a weight loss supplement, pharmaceutical therapy, brown adipose tissue modulation (e.g., controlled activation, enhanced differentiation, supplemental implantation, etc.), pharmaceutical administration, electrical stimulation of nerves that innervate at least a portion of the gastrointestinal tract, therapies impacting circadian rhythms, bile acid modulation, intestinal mucus production and metabolism, gastric bypass, duodenojejunal bypass, biliopancreatic diversion, vertical sleeve gastrectomy, adjustable gastric banding, vertical banded gastroplasty, intragastric balloon therapy, gastric plication, Magenstrasse and Mill, small bowel transposition, biliary diversion, duodenal endoluminal barrier, or similar manipulations of the gastrointestinal tract. In one embodiment, the composition can be delivered at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 days or more before the treatment. In another embodiment, the composition can be delivered at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 days or more after the treatment. In yet another embodiment, the composition can be delivered concurrently with the therapeutic treatment. In another embodiment, the composition can be delivered for a treatment period that lasts until the desired outcome (e.g., weight loss, diabetes improvement, target population has been achieved, the target population has been maintained, etc.) is achieved.

Delivery of the microbiota composition can also be repeated one or more times. The repeated delivery of the microbiota composition can be one or more times before and/or after a metabolic disorder treatment. The repeated delivery can be in a manner similar to the initial delivery.

The microbiota composition can also be administered with agents that may include therapeutic, prophylactic, or diagnostic agents selected from small molecules, nucleic acids, proteins, prebiotics like polypeptides, prebiotics including bacterial components such as bacterial cell wall components such as peptidoglycan, bacterial nucleic acids such as DNA and RNA, bacterial membrane components, and bacterial structural components such as proteins, carbohydrates, lipids and combinations of these such as lipoproteins, glycolipids and glycoproteins, bacterial metabolites, organic acids, inorganic acids, bases, proteins and peptides, enzymes and co-enzymes, amino acids and nucleic acids, carbohydrates, lipids, glycoproteins, lipoproteins, glycolipids, vitamins, bioactive compounds, metabolites containing an inorganic component, and small molecules such as nitrous molecules or molecules containing a sulphurous acid, resistant starch, potato starch or high amylose starch, modified starches (including carboxylated starches, acetylated, propionated, and butyrated starches), non-digestible oligosaccharides such as fructooligosaccharides, glucooligosaccharides, xylooligosaccharides, galactooligosaccharides, arabinoxylans, arabinogalactans, galactomannans, polydextrose, oligofructose, inulin, derivatives of these, but not excluding other oligosaccharides able to exert prebiotic effects, other soluble fibers, and combinations thereof. In one embodiment, the agent delivered is a small molecule delivered that has low oral bioavailability and acts on a microbial niche of the host's gut. Low oral bioavailability is generally undesirable in drugs, since absorption through the intestine is an objective of most oral therapies.

The microbiota composition can also be administered in the same composition with compounds or agents as described above or can be administered individually with the compounds or agents administered before, concurrent with, and/or after the microbiota compositions. The microbiota composition can be administered at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 days or more prior to the administration of compounds or agents. The microbiota composition can also be administered at least about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31 days or more after the administration of compounds or agents. The microbiota composition can be administered concurrently with the administration of compounds or agents.

The composition can also be delivered by a system that can be at least partially implantable. The implantable system can be any of those known and used in the art. The system can include a programmable pump such as those commonly used to deliver insulin to a diabetic patient. One or more of these components may be modular and connected to a transcutaneous delivery system which may include a port, needle, patch, or the like. In an exemplary embodiment, the implantable system includes a reservoir and a port. The reservoir may include a refillable or reloadable container for holding the composition. In another embodiment, the system can include a catheter. In another embodiment, the implantable system is a translumenal catheter. The system can also be configured to deliver the composition at a prescribed dosage and/or a prescribed interval. The prescribed dosage and/or prescribed interval can be determined by those of skilled in the art.

One skilled in the art will appreciate further features and advantages of the invention based on the above-described embodiments. Accordingly, the invention is not to be limited by what has been particularly shown and described in the examples or figures, except as indicated by the appended claims. All publications and references cited herein are expressly incorporated herein by reference in their entirety.

EXAMPLES

Example 1

Materials and Methods

Animals.

Male C57BL/6J diet-induced obese (DIO) mice were purchased at 22-26 weeks of age from Jackson Laboratories. These mice were maintained on a 60% high fat diet (HFD; Research Diets, D12492, New Brunswick, N.J.) from 6 weeks of age until they reached a surgical weight of 40-50 grams. All animal studies were performed in accordance with the Massachusetts General Hospital Subcommittee on Research Animal Care guidelines and used under an approved protocol. Male, age-matched (7-10 weeks old), germ-free Swiss Webster mice were obtained from Taconic and used under an approved Harvard Medical School IACUC protocol.

Animals in the RYGB group were fasted overnight and anesthetized with isofluorane. The abdomen was exposed and a single transection was made just distal to the ligament of Treitz. The proximal intestinal portion (the biliopancreatic (BP) limb) was re-anastamosed to a jejunal segment ~9 cm (6 Q-tips) distal to the transection to create the "Y" junction. The glandular and non-glandular portion of the stomach was double-sutured and transected to form the stomach remnant and stomach pouch, respectively. An incision was made at the stomach pouch and the distal segment of the transection intestine (proximal Roux (Rx) limb) was anastamosed to the stomach. All anastamoses were double-checked for leakage prior to body wall and subcutaneous closures.

Figure 2:
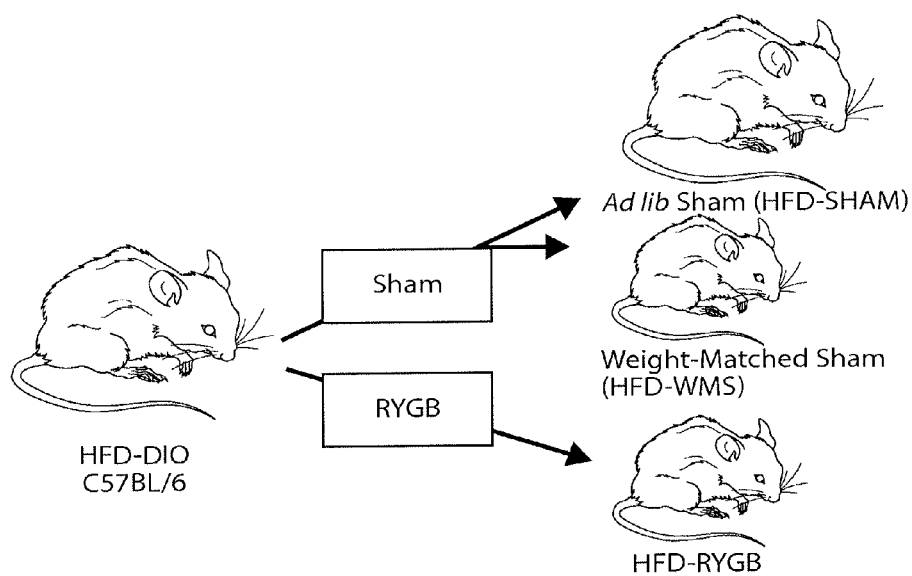
FIG. 2 is a diagram showing the procedure used to generate the experimental animals. In particular, mice were separated into three groups, animals that underwent surgical gastric bypass and maintained on high fat diet (RYGB), animals that underwent sham surgery and maintained on high fat diet (SHAM), and animals that underwent sham surgery and were calorically restricted to weigh the same as the RYGB animals, i.e., weight matched (WMS)

Sham-operated animals (SHAM) were treated in a similar manner as the RYGB animals pre-operatively, and the same intestinal transection-anastomosis was performed. The stomach was manipulated in a similar manner as the RYGB animals, but no transections or incisions were made of the stomach. See FIG. 2.

All animals were given 0.05 mg/kg buprenorphine IM for prevention and/or relief of post-operative pain. After surgery, animals were housed individually on wire floors and maintained on liquid diet (Vital HN, Abbott Labs, Columbus, Ohio) for up to 2 weeks until fully weaned back onto high fat diet (HFD). Body weights were monitored weekly. Three weeks post-operatively, a group of weight-stabilized SHAM animals were randomly chosen and maintained on a daily restricted diet of ~⅓ of the RYGB daily food intake in order to reduce and maintain body weight to a normal weight of ~30-33 grams to match the weight of the RYGB animals (weight-matched sham group; WMS). See FIG. 2. For indirect calorimetry experiments, animals were fed a powdered, irradiated form of Mouse Diet 9F (Labdiet 5020).

Fecal Sampling and Processing.

Weekly fecal samples were collected directly into DNase- and RNase-free tubes and stored at −80° C. until processed. DNA was extracted using the PowerSoil bacterial DNA extraction kit (MoBio, Carlsbad Calif.) and PCR-amplified using universal bacterial primers targeting variable region 4 of the 16S rRNA gene with the following thermocylcer protocol: Denature at 94° C. for 3 min, 35 cycles of 94° C. for 45 sec, 50° C. for 30 sec, and 72° C. for 90 sec, with final annealing temperature at 72° C. for 10 min. Triplicate reactions for each sample were pooled and amplification was confirmed with gel electrophoresis on a 1.5% agarose gel. 16S rRNA DNA amplicons were cleaned with the Ampure XP kit (Agencourt, Danvers, Mass.) and quantified using the Quant-iT Picogreen ds DNA Assay Kit (Invitrogen, Carlsbad, Calif.). Amplicons were sequenced with the Illumina Hi-Seq platform. Multivariable statistical analysis was used to compare microbial composition among the treatment groups. 16S rRNA gene sequences were analyzed using the QIIME software package (Quantitative Insights Into Microbial Ecology) in addition to custom Perl scripts to analyze alpha (within sample) and beta (between sample) diversity.

Food Intake and Fecal Analysis.

A subgroup of animals was used for food intake and fecal analysis. Animals were housed individually on wire floors. Food was weighed every other day and adjusted for spillage. All fecal pellets were collected, weighed, and submitted to the University of Arkansas for fecal calorimetry, crude fat, and crude nitrogen. Sample amount permitting, fecal pH was also measured.

Tissue Harvest and Intestinal Axis Sampling.

Animals were sacrificed between 12 and 15 weeks after surgery. Prior to euthanization, animals were fasted for 2 hours, and a blood glucose level was measured from the tail tip using a handheld glucometer (Alpha-Trak, Abbott Labs; Abbott Park, Ill.), anesthetized with 100 mg/kg IP sodium pentobarbital and euthanized by cardiac exsanguination. Blood was collected in EDTA-containing tubes and plasma was stored at −80° C. The following intestinal sections were collected for bacterial DNA analysis: stomach pouch, stomach remnant, BP limb, Roux limb, common limb (first 3 cm distal to BP/Rx anastomosis), the distal ileum, ½ cecum, and colon. Sections representative of each limb were also collected in SHAM and WMS animals. Each section was flushed with extraction buffer (200 mM NaCl, 200 mM Tris, 20 mM EDTA, pH 8.0) to retrieve luminal bacterial contents. Each section was then cut longitudinally and the mucosa scraped off with ethanol-cleaned microscope slides to obtain mucosal adherent bacteria samples. Collection of ceca and colons were performed separately from the rest of the intestine to avoid contamination. All contents and mucosal adherent samples were flash frozen in liquid nitrogen and stored at −80° C. until DNA extraction with the same PowerSoil DNA extraction kit mentioned above. In another subgroup of animals, pH was measured in different segments of the gastrointestinal tract, using a pH meter connected to a micro pH electrode (Thermo Scientific, Rochester, N.Y.). In addition to intestinal sampling, epididymal and retroperitoneal fat pads were collected and weighed as a biomarker for visceral adiposity. Whole body lean and fat mass were determined by NMR (Bruker TD Minispec, Billerica, Mass.).

Biochemical Assays.

Plasma insulin was measured using the mouse ultrasensitive insulin ELISA (Alpco, Salem, N.H.). Fasting TG and non-esterified fatty acids (NEFAs) were assayed from serum using their respective kits (Wako Chemical, Richmond, Va.). Liver triglycerides were extracted with overnight incubation in ethanolic KOH at 55° C., and free glycerol was measured using free glycerol reagent (Sigma, Saint Louis, Mo.). Plasma leptin was measured by ELISA (Crystal Chem, Inc., Downers Grove, Ill.).

Germ-Free Mouse Experiments.

A donor animal from each group—RYGB, sham operated (SHAM), and non-operated diet induced obese (DIO) mice—was treated in the same way as all other mice, except that the cecal contents were saved and mixed in reduced anaerobic PBS buffer. The sample was homogenized in an anaerobic chamber, and the resultant slurry administered by oral gavage to germ-free, 7-13 week old, male Swiss Webster recipient mice (5-6 animals/group). Animals were housed 1-2/cage on wire floors and fed autoclaved rodent breeder chow. A group of uninoculated mice were used as a control. Body weights and cumulative food intake were recorded weekly during the 2-week colonization period. Fecal pellets were collected at days −1, 1, 2, 3, 7, and 13 after gavage. On day 13, food was withheld from animals overnight. On day 14, animals were removed from the microisolators and transferred to a procedure room, where a fasting blood glucose was taken with a handheld glucometer (Alpha-trak, Abbott Labs) from blood taken from the tail tip. Animals were anaesthetized with isofluorane. A terminal blood collection was taken, tissues harvested, and liver and visceral (retroperitoneal and epididymal) fat pads were weighed.

Doubly Labeled Water.

Doubly=labeled water was made using a 3:1 dilution of O-18 water (97%; Cambridge Isotope Laboratories, Andover, Mass.; OLM-240-97-1) and deuterium oxide (Sigma, #151882-10G), sterile filtered, and stored in ethylene oxide sterilized amber injection bottles with crimped lids. A pre-injection baseline sample was collected 1-2 days prior to the experiment. Following oral gavage of donor sample microbiota, animals were injected with 60 μL (66 μg) of doubly-labeled water tracer IP and the time of injection was recorded. A post-injection blood sample was collected between 60-90 minutes following injection and used as the maximum equilibrated tracer dilution. Blood samples were then collected at days 5, 8, and 14 following injection. Times were precisely recorded with each blood sample collection. Blood samples were centrifuged at 10,000 rcf for 5 minutes to separate plasma and stored at −80 C until analysis. Samples from days −1, 0, 5, and 8 were sent to Metabolic Solutions (Andover, Mass.) for tracer analysis.

To determine the rate of $CO_2$ production ($rCO_2$), the log of the deuterium and O-18 levels of blood samples from each animal were plotted against time to retrieve a linear slope, representing the rate of tracer elimination from the body pool. These samples were compared with an international standard (Vienna Standard Mean Ocean Water). The rate of CO2 production (rCO2) was calculated based on modified equations of Speakman, Nair, and Goran (Am J Physiol 264:E912-E917, 1993):

$$rCO_2 = (N/2.196) \times (k_o - 1.0472 k_d) \text{ where } N = [(N_o) + (N_d/1.0427)]/2$$

The estimate of energy expenditure was calculated with an RQ estimate of 0.85. Total body water was determined based on the mean pool sizes for deuterium and oxygen-18.

Indirect Calorimetry.

Animals were transported in sterile containers prior to placement in a 16 cage CLAMS (Comprehensive Lab Animal Monitoring System; Columbus, Ohio) and left to sit for 1 hour prior to start of measurements. Flow rate was set to 0.6 L/min. Animals were checked daily for food and water; two animals required refilling of food. One GF-R animal chewed much of the food into the spillage bucket and required refills during both days; an error in re-balancing the food weigh scale produced an artificial increase in food intake. Thus, the animal's food intake data was taken out of the study.

Short Chain Fatty Acid Analysis.

Cecal content samples were kept frozen at −80° C. until analysis. The samples were removed from the freezer and weighed, and 500 μL of water (HPLC grade) was added to each of the thawed samples. The samples were vortexed for 1 minute until the material was homogenized. The pH of the suspension was adjusted to 2-3 by adding 50 μL of 50% sulfuric acid. The acidified samples were kept at room temperature for 5 minutes and vortexed briefly every minute. The samples were then centrifuged for 10 minutes at 5000 g. 400 μL of the clear supernatant was transferred into an Eppendorf tube for further processing. For the volatile extraction, 50 μL of the internal standard (1% 2-methyl pentanoic acid solution) and 400 μL of ethyl ether anhydrous were added. The tubes were vortexed for 30 seconds and then centrifuged at 5000 g for 10 minutes. 1 μL of the upper ether layer was injected into the chromatogram for analysis and compared with an internal standard control solution containing 10 mM of acetic, propionic, isobutyric, butyric, isovaleric, valeric, isocaproic, caproic, and heptanoic acids (Matreya, Pleasant Gap Pa.).

Chromatographic analysis was carried out using a Shimadzu GC14-A system with a flame ionization detector (FID) (Shimadzu Corp, Kyoto, Japan). A fused silica capillary column 30 m×0.25 mm coated with 0.25 um film thickness was used (Nukol™) for the volatile acids (Supelco Analytical, Bellefonte, Pa.). Nitrogen was used as the carrier gas. The oven temperature was 170° C. and the FID and injection port was set to 225° C. The injected sample volume was 1 μL and the run time for each analysis was 10 minutes. The chromatograms and data integration was carried out using a Shimadzu C-R5A Chromatopac. The retention times and peak heights of the acids in the standard mix were used as references for the sample unknowns. These acids were identified by their specific retention times and the concentrations determined and expressed as mM concentrations per gram of sample.

RNA Extraction and qPCR.

RNA was extracted from most tissues with Trizol (Invitrogen, Carlsbad, Calif.). Adipose tissue RNA was extracted using the lipid tissue RNeasy Qiagen kit (Valencia, Calif.). 1 μg of RNA was used for cDNA amplification, using the SuperScript III First-Strand Synthesis System and random hexamer primers under manufacturer instructions (Invitrogen, Carlsbad, Calif.). qPCR was performed with 50 ng of cDNA using inventoried primers from Applied Biosystems (Carlsbad, Calif.). Gene expression was analyzed by the $\Delta\Delta C_T$ method (Applied Biosystems Bulletin #2) with the appropriate control condition as calibrator. Beta-actin was used as a housekeeping gene.

Statistical Analysis.

For in vivo physiology experiments, all data are expressed as means±SEM. Statistics were performed using GraphPad Prism (v. 5). Significance was accepted at $P<0.05$.

Example 2

Donor Analysis

Mice were separated into three groups: animals that underwent surgical gastric bypass and maintained on high fat diet (RYGB), animals that underwent sham surgery and maintained on high fat diet (SHAM), and animals that underwent sham surgery and were weight matched to the RYGB animals (WMS). See FIG. 2.

Figure 3A:
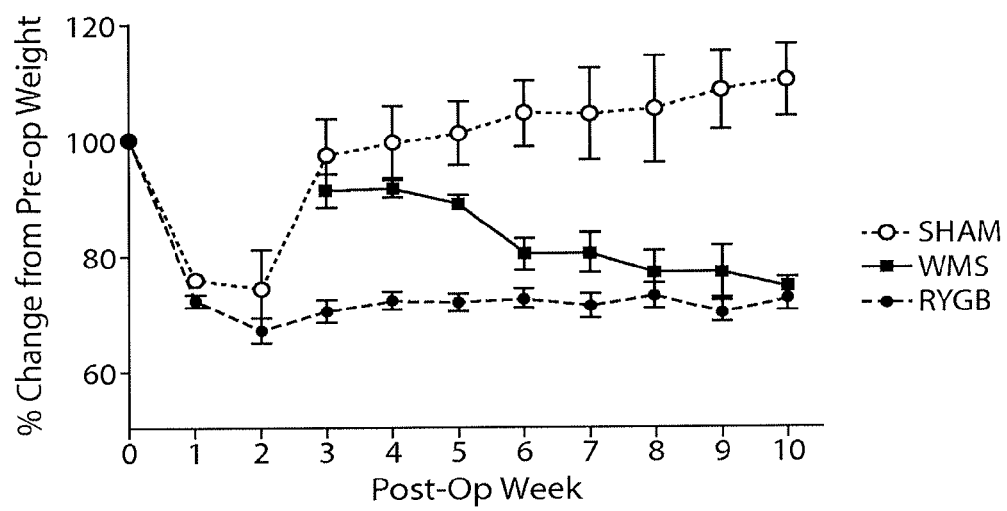
FIG. 3A is a graph of the change in body weights over time of the RYGB, SHAM, and WMS animals after gastric bypass or sham operation as compared to pre-operative weights.

Animals were weighed weekly and their weights were compared to pre-operative weights. FIG. 3A shows the percent change of the pre-operative weights for the three groups of mice every week until 10 weeks post-surgery. The weights in the SHAM group steadily increased to greater than pre-surgery weights. RYGB group and WMS group significantly lowered weights post-surgery. The RYGB group decreased to approximately 70% of pre-surgery weights after 2 weeks, whereas the WMS group steadily decreased until 10 weeks post-surgery. Complete weight-matching occurred and was stabilized by 6 weeks post-surgery (3 weeks after food restriction).

similar levels to those of low fat diet animals. There is a significant improvement in insulin sensitivity in the RYGB group relative to the SHAM group, as indicated by homeostatic model assessment for insulin resistance (HOMA-IR).

TABLE 2

2-hour Fasted Blood Concentrations.

|  | RYGB | SHAM | WMS | DIO | LF |
|---|---|---|---|---|---|
| N | 17 | 6 | 6 | 8 | 3 |
| Glucose (mg/dL) | $137 \pm 6.9^A$ | $172 \pm 8.7^B$ | $143 \pm 8.8^A$ | $209 \pm 11.1$ | $122 \pm 2.0$ |
| Insulin (ng/mL) | $2.18 \pm 0.39^A$ | $5.28 \pm 2.0^B$ | $0.35 \pm 0.05^C$ | $25.0 \pm 5.10$ | $2.31 \pm 0.89$ |
| HOMA-IR | $18.3 \pm 3.2^A$ | $57.2 \pm 21.6^B$ | $3.0 \pm 0.48^C$ | $317.7 \pm 64.8$ | $17.4 \pm 6.7$ |
| Tg (mg/dL) | $35.4 \pm 7.1^A$ | $75.4 \pm 35.3^A$ | $20.9 \pm 2.4^A$ | $25.0 \pm 2.2$ | $63.7 \pm 19.3$ |
| NEFA | $0.18 \pm 0.02^A$ | $0.19 \pm 0.03^A$ | $0.11 \pm 0.02^B$ | $0.23 \pm 0.01$ | $0.15 \pm 0.03$ |

Values are represented as means ± SEM.
Data not annotated by the same letter are significantly different (P < 0.05, ANOVA).

TABLE 1

One-week food intake and fecal calorimetry analysis.

|  | RYGB | SHAM | WMS |
|---|---|---|---|
| N | 14 | 11 | 6 |
| Total output (g) | $5.2 \pm 0.37^A$ | $2.7 \pm 0.08^B$ | $2.2 \pm 0.13^B$ |
| Fecal kcal/g | $5.4 \pm 0.11^A$ | $3.4 \pm 0.04^B$ | $3.4 \pm 0.11^B$ |
| Fecal Fat % | $24.5 \pm 2.3^A$ | $0.5 \pm 0.09^B$ | $1.0 \pm 0.52^B$ |
| Fecal Nitrogen % | $2.3 \pm 0.14^A$ | $2.6 \pm 0.21^A$ | $2.3 \pm 0.32^A$ |
| Fecal pH | $7.0 \pm 0.09^A$ | $8.0 \pm 0.04^B$ | $8.3 \pm 0.20^B$ |
| Food intake (kcals) | $121.9 \pm 4.2^A$ | $114.1 \pm 2.1^A$ | $86.92 \pm 1.6^B$ |
| Fecal energy (kcals) | $28.6 \pm 2.4^A$ | $9.1 \pm 0.3^B$ | $7.7 \pm 0.5^B$ |
| Net Energy$_{in}$ (kcals) | $93.2 \pm 2.5^A$ | $105.0 \pm 1.8^B$ | $79.3 \pm 1.3^C$ |
| Fat intake (g) | $8.14 \pm 0.28^A$ | $7.63 \pm 0.14^A$ | $5.81 \pm 0.11^B$ |
| Fecal Fat (g) | $1.36 \pm 0.19^A$ | $0.02 \pm 0.01^B$ | $0.03 \pm 0.01^B$ |
| Net Fat$_{in}$ (g) | $6.78 \pm 0.16^A$ | $7.61 \pm 0.14^B$ | $5.78 \pm 0.10^A$ |
| N intake (g) | $6.05 \pm 0.21^A$ | $5.67 \pm 0.10^A$ | $4.31 \pm 0.08^B$ |
| Fecal N (g) | $0.12 \pm 0.01^A$ | $0.07 \pm 0.004^B$ | $0.05 \pm 0.01^B$ |
| Net Nitrogen$_{in}$ (g) | $5.92 \pm 0.20^A$ | $5.59 \pm 0.10^A$ | $4.26 \pm 0.08^B$ |

Values represented as means ± SEM.
Data not annotated by the same letter are significantly different (P < 0.05 ANOVA).

As shown in Table 1, the RYGB group had a net energy intake lower than the SHAM group and higher than the WMS group.

Figure 3B:
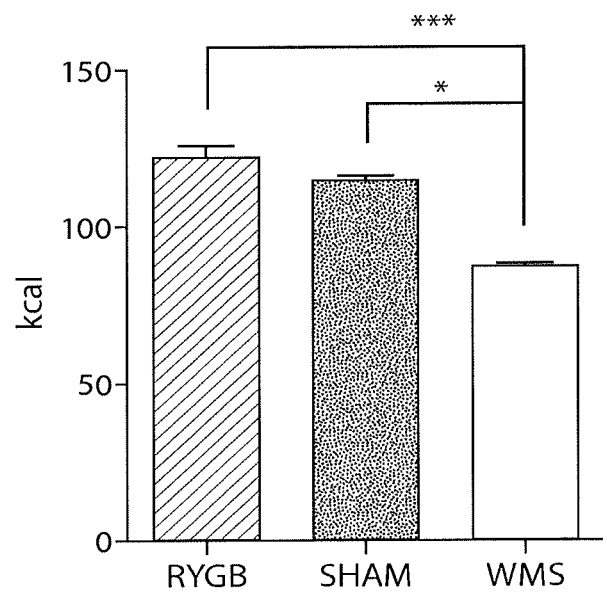
FIG. 3B is a bar graph showing one week cumulative food intake of a group of RYGB, SHAM, and WMS animals after gastric bypass or sham operation.
Figure 3C:
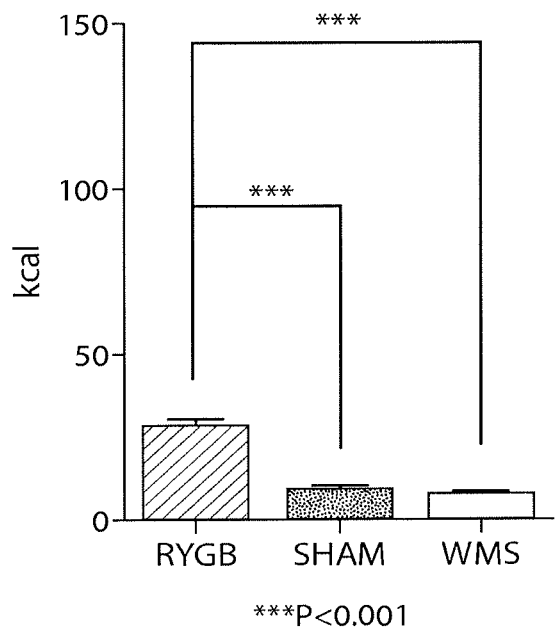
FIG. 3C is a bar graph showing one week cumulative fecal energy output of the RYGB, SHAM, and WMS animals from FIG. 3B.
Figure 3D:
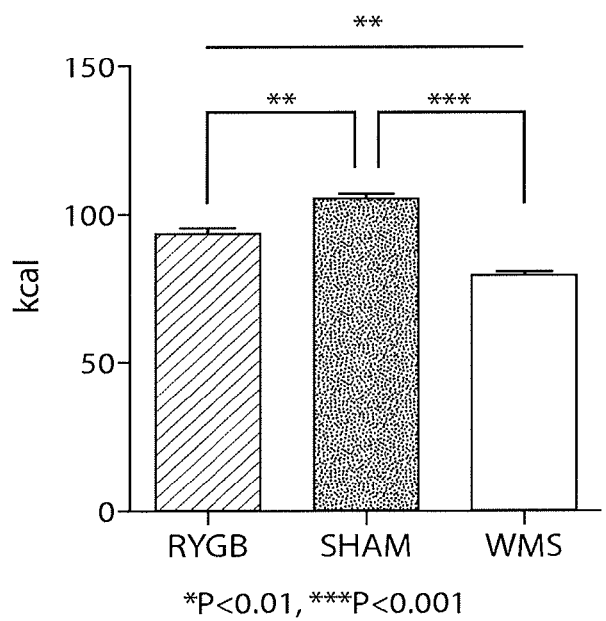
FIG. 3D is a bar graph showing net energy intake of the RYGB, SHAM, and WMS animals from FIG. 3B over a one week period.

FIG. 3B shows food intake of the three groups. Asterisks are used to identify statistically significant differences. Food intake in the RYGB group was not significantly different from the SHAM group, whereas the WMS group was fed ~25% less food in order to match the weight of the RYGB group. The RYGB group lost significantly more energy in their feces than both the SHAM group and the WMS group. See FIG. 3C. FIG. 3D shows the net energy intake for each group, which was calculated as the difference between the food intake and the fecal energy output. The net energy intake of the RYGB group was significantly lower than the net energy intake of the SHAM group and significantly higher than the net energy intake of the WMS group. See FIG. 3D.

Figure 3E:
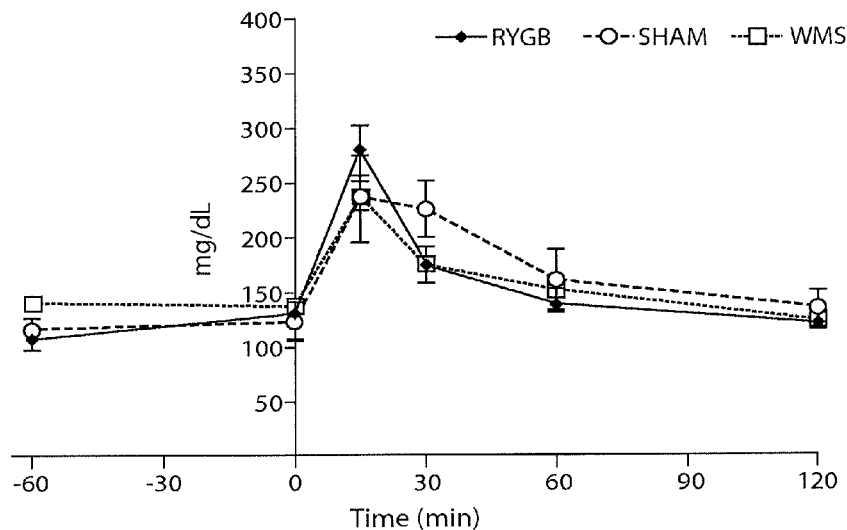
FIG. 3E is a graph of the change in oral glucose tolerance over time of the RYGB, SHAM, and WMS animals after gastric bypass or sham operation.
Figure 3F:
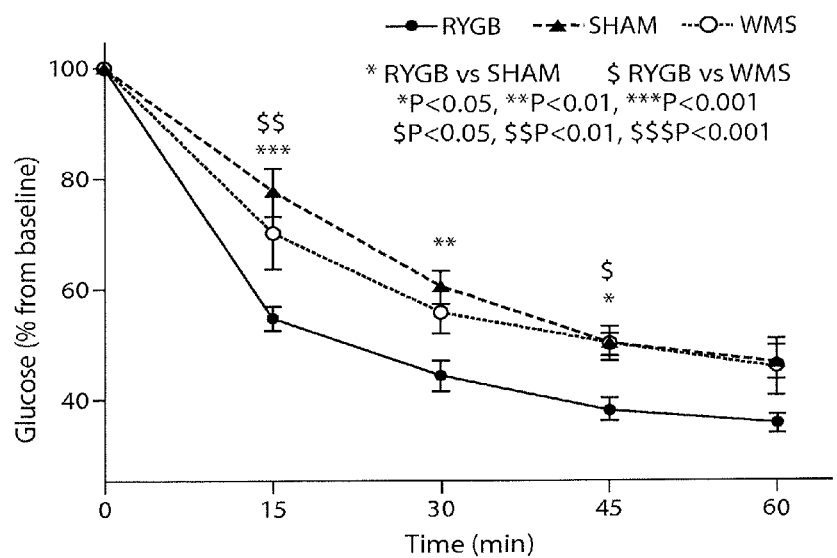
FIG. 3F is a graph of the change in insulin tolerance over time of the RYGB, SHAM, and WMS animals after gastric bypass or sham operation.

As shown in Table 2, RYGB mice maintained on a high fat diet exhibited lower plasma glucose and insulin levels at 15 weeks post-surgery, as compared to SHAM animals, and Glucose tolerance and insulin tolerance were measured from the three groups of mice at 15 weeks post-surgery. FIG. 3E shows an improvement in oral glucose tolerance between the RYGB and WMS groups versus the SHAM group. FIG. 3F shows a significant improvement in insulin sensitivity in the RYGB group as compared to the SHAM and WMS groups.

Figure 4:
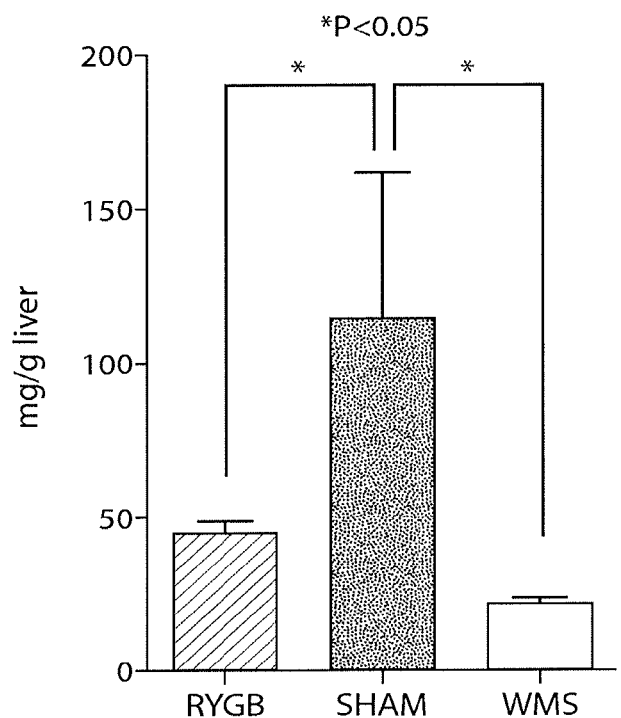
FIG. 4 is a bar graph showing the level of liver triglycerides in the RYGB, SHAM, and WMS animals measured at the time of tissue harvest.
Figure 5:
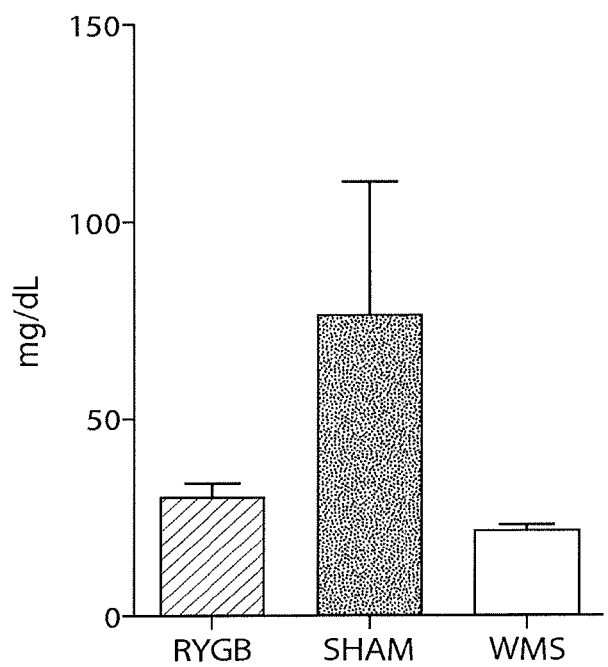
FIG. 5 is a bar graph showing the level of serum triglycerides in the RYGB, SHAM, and WMS animals measured at the time of tissue harvest.

Triglyceride levels were measured in both liver and serum for animals in each group. SHAM animals had higher triglycerides in both the liver (FIG. 4) and serum (FIG. 5) than RYGB and WMS animals.

Figure 6:
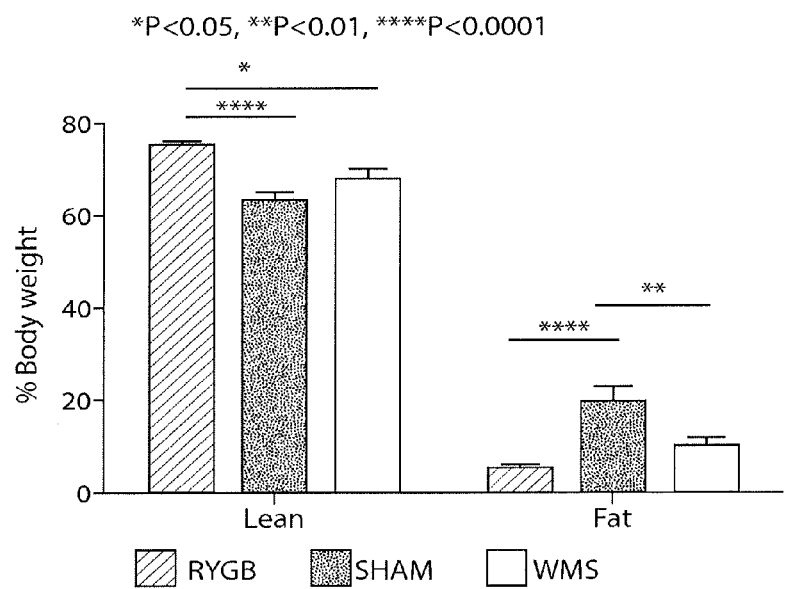
FIG. 6 is a bar graph showing the percentage of lean and fat weights of RYGB, SHAM, and WMS mice as compared to total body weight at the time of tissue harvest.

Body composition was determined from whole body lean and fat mass from the three groups of mice post mortem at 12-15 weeks after surgery. FIG. 6 shows the RYGB group had significantly less fat mass than the SHAM group. The RYGB group also has greater lean mass than both WMS and SHAM groups.

Figure 7:
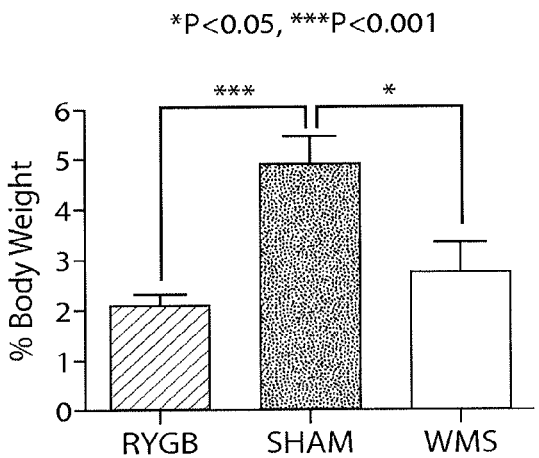
FIG. 7 is a bar graph showing the percentage of adipose tissue found in the epididymal and retroperitoneal fat pad of the RYGB, SHAM, and WMS animals as compared to total body weight at the time of tissue harvest.

In addition, the adiposity index was determined from epididymal and retroperitoneal fat pads collected from animals of the three groups. Both RYGB and WMS groups had significantly lower percentage of adiposity than the SHAM group. See FIG. 7.

Example 3

Donor Microbiota Profiles

Figure 8:
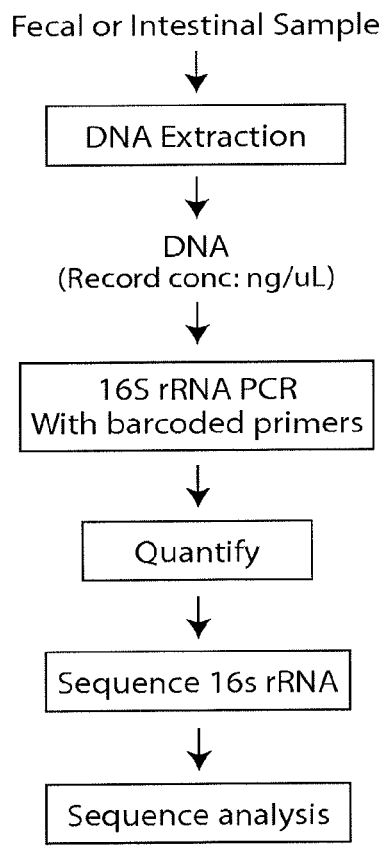
FIG. 8 is a flow diagram showing the analysis of microbiota in fecal samples from from animals.

Fecal samples were collected post-surgery from animals in the three groups every week to measure temporal effects of gastric bypass on overall microbial diversity. FIG. 8 diagrams the protocol that was used for analysis of the fecal samples.

Figure 9:
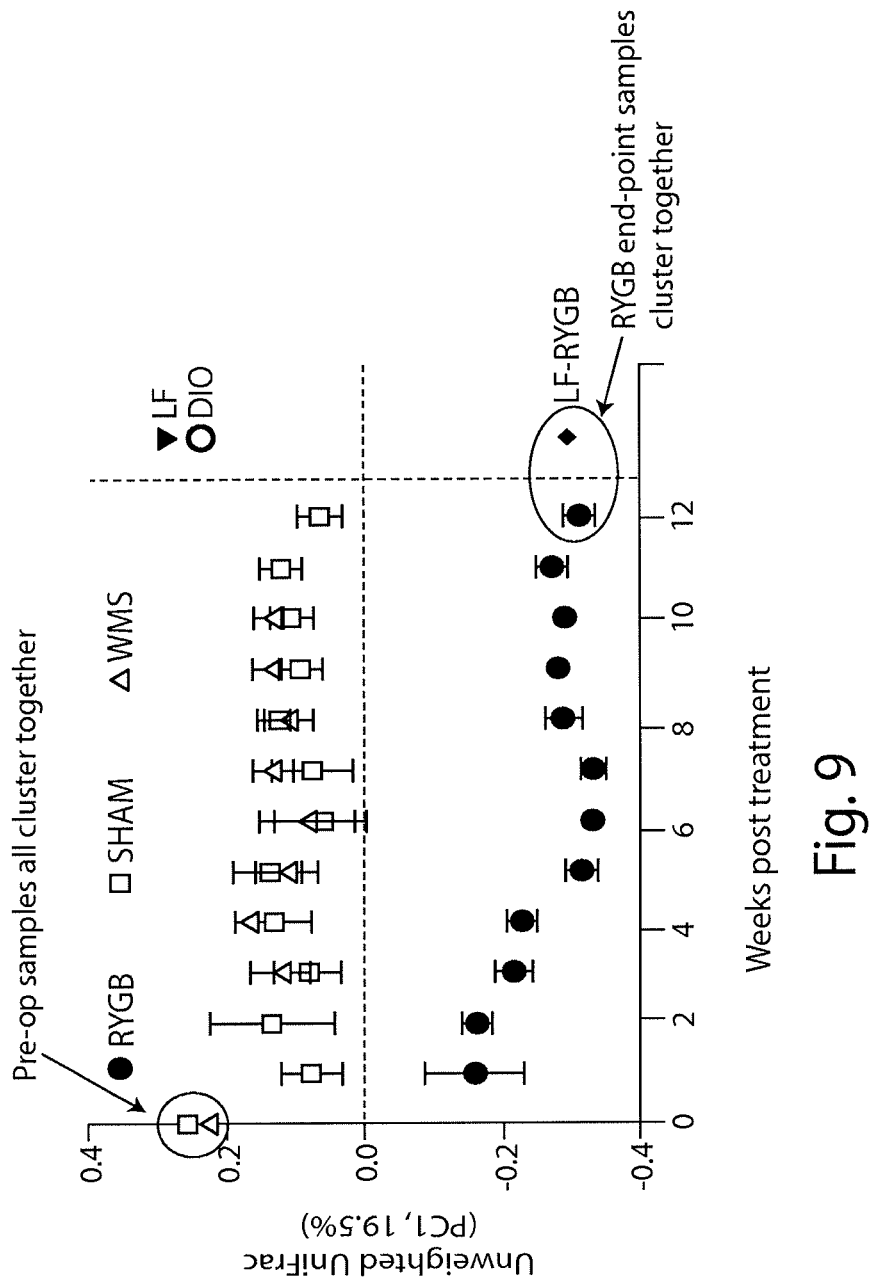
FIG. 9 is a graph showing the first principal coordinate analysis (PC1) from an Unweighted UniFrac-based analysis comparing fecal microbial communities of the animals.

The microbial diversity was compared in samples of isolated bacterial DNA obtained from contents of the gastric stomach, distal stomach remnant, BP limb, Rx limb, common limb (first 3 cm distal to BP/Rx anastomosis), the distal ileum, ½ cecum, and colon. Bacterial DNA from the samples was analyzed by an unweighted UniFrac analysis of the principal coordinate (PC) for surgery. FIG. 9 shows the UniFrac-based analysis showing the change in microbial populations in animals before and after RYGB or sham operation. Clustering of the sample coordinates indicates similar microbial ecologies prior to surgery, with a marked shift in the RYGB communities within a week after surgery that continued over time and stabilized after 5 weeks.

Interestingly, the sham surgery had a small but equivalent effect in the fecal microbial populations, independent of food restriction. Furthermore, the differences in microbial ecology between SHAM and WMS groups were minimal. Samples from donors that received gastric bypass maintained on high fat diet (RYGB) and animals that received gastric bypass maintained on low fat diet (LF-RYGB) clustered together, suggesting that the effect of surgery on shaping the gut microbial communities is independent of diet. See FIG. 9.

Figure 10:
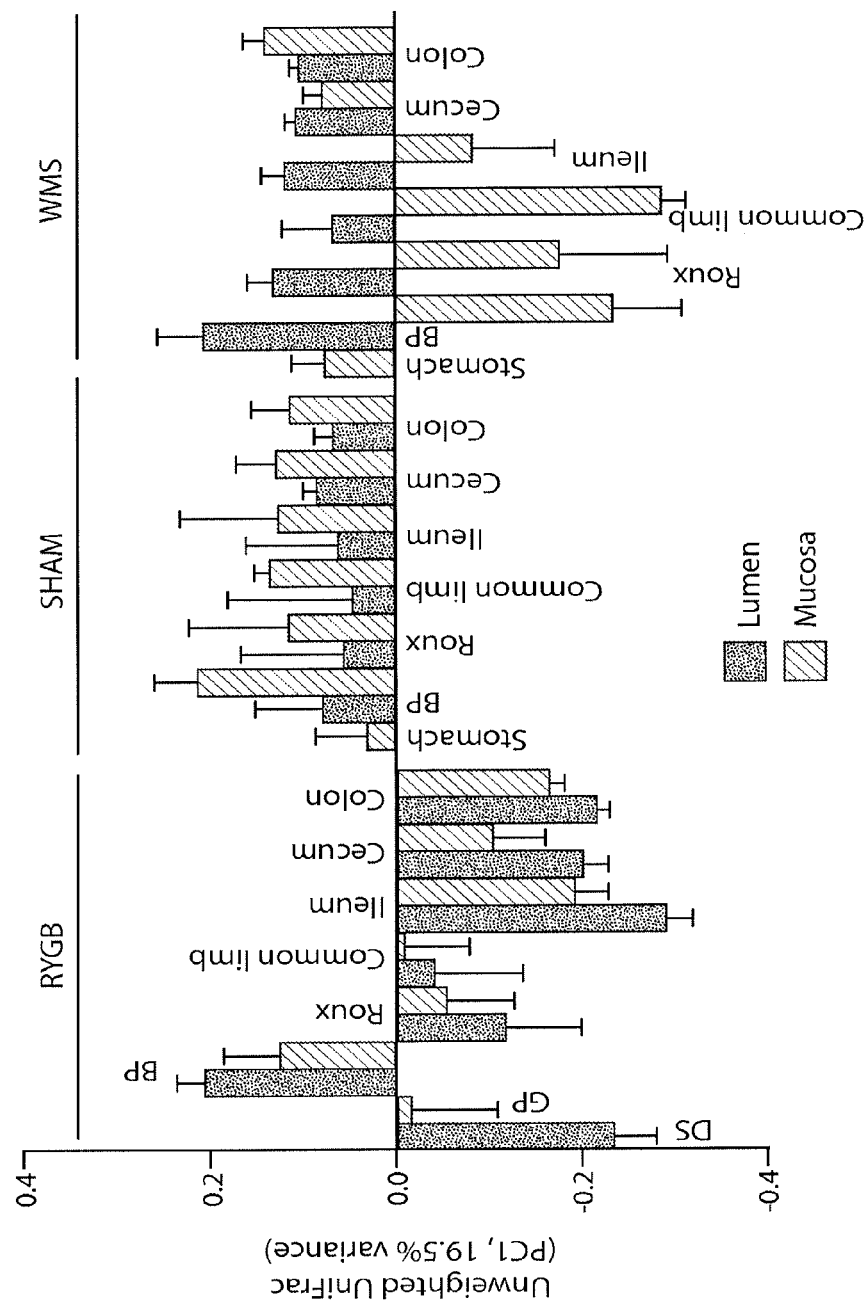
FIG. 10 is a graph showing an unweighted UniFrac-based analysis comparing microbial populations found in lumen and mucosa of the distal stomach remnant/gastric pouch (DS/GP), biliopancreatic limb (BP), Roux limb (Roux), common limb (CL), ileum, cecum, or colon of the animals.

UniFrac population comparison is shown in FIG. 10 of the three treatment groups for each of the locations from which microbial contents were collected: gastric pouch, distal stomach remnant, BP limb, Rx limb, common limb (first 3 cm distal to BP/Rx anastomosis), the distal ileum, ½ cecum, and colon indicating the location along the length of the intestinal tract at which the greatest changes in microbial ecology occur (distal segments: ileum, cecum, colon; and stomach remnant; both luminal content and mucosal adherent populations) after RYGB. There is also evidence of changes in the microbial communities of mucosal adherent colonies along the entirety of the small intestine (BP, Roux, common limb, and ileum) in WMS animals. The linear discriminant analysis (LDA) effect size (LEfSe) method was used to identify bacterial taxa and species-level phenotypes whose relative abundance varied significantly among fecal samples taken from the RYGB, SHAM, and WMS groups. An LDA score>2 shows significant variation. As shown in Table 3, there was a significant increase in *Alistipes* and *Akkermansia* after RYGB throughout the gastrointestinal tract.

TABLE 3

Taxonomic Groups with Differential Relative Abundance Between Treatments

| Taxonomic group | | | | | | Association | LDA score |
|---|---|---|---|---|---|---|---|
| p_Bacteroidetes | c_Bacteroidia | o_Bacteroidales | | | | RYGB | 2.65 |
| p_... | c_... | o_... | f_Rikenellaceae | | | RYGB | 2.65 |
| p_... | c_... | o_... | f_... | g_Alistipes | | RYGB | 2.65 |
| p_... | c_... | o_... | f_... | g_... | s_Alistipesfinegoldii | RYGB | 2.10 |
| p_... | c_... | o_... | f_... | g_... | s_Alistipesfinegoldii.109956 | RYGB | 2.10 |
| p_Firmicutes | c_Clostridia | o_Clostridiales | f_Clostridiaceae | | | RYGB | 2.10 |
| p_... | c_... | o_... | f_... | g_Clostridium | | RYGB | 2.10 |
| p_... | c_... | o_... | f_... | g_... | s_Clostridiumperfringens | RYGB | 2.42 |
| p_... | c_... | o_... | f_... | g_... | s_Clostridiumperfringens.46789 | RYGB | 2.42 |
| p_Proteobacteria | c_Gammaproteobacteria | | | | | RYGB | 2.34 |
| p_... | c_... | o_Enterobacteriales | | | | RYGB | 2.37 |
| p_... | c_... | o_... | f_Enterobacteriaceae | | | RYGB | 2.34 |
| p_... | c_... | o_... | f_... | g_Escherichia | | RYGB | 2.34 |
| p_... | c_... | o_... | f_... | g_... | s_ | RYGB | 2.13 |
| p_... | c_... | o_... | f_... | g_... | s_169182 | RYGB | 2.13 |
| p_Verrucomicrobia | c_Verrucomicrobiae | o_Verrucomicrobiales | | | | RYGB | 2.27 |
| p_... | c_... | o_... | f_Verrucomicrobiaceae | | | RYGB | 2.27 |
| p_... | c_... | o_... | f_... | g_Akkermansia | | RYGB | 2.27 |
| p_... | c_... | o_... | f_... | g_... | s_ | RYGB | 2.27 |
| p_... | c_... | o_... | f_... | g_... | s_178399 | RYGB | 2.77 |
| p_Firmicutes | c_Bacilli | o_Lactobacillales | | | | SHAM | 2.22 |
| p_... | c_... | o_... | f_Lactobacillaceae | | | SHAM | 2.22 |
| p_... | c_... | o_... | f_... | g_Lactobacillus | | SHAM | 2.17 |
| p_Tenericutes | | | | | | SHAM | 2.17 |
| p_... | c_Erysipelotrichi | | | | | SHAM | 2.42 |
| p_... | c_... | o_Erysipelotrichales | | | | SHAM | 2.42 |
| p_... | c_... | o_... | f_Erysipelotrichaceae | | | SHAM | 2.42 |
| p_... | c_... | o_... | f_... | g_Allobaculum | | SHAM | 2.41 |
| p_... | c_... | o_... | f_... | g_... | s_AllobaculumspID4 | SHAM | 2.13 |
| p_... | c_... | o_... | f_... | g_... | s_AllobaculumspID4.115098 | SHAM | 2.09 |
| p_Bacteroidetes | c_Bacteroidia | o_Bacteroidales | f_ | | | WMS | 2.54 |
| p_... | c_... | o_... | f_... | g_ | | WMS | 2.54 |
| p_... | c_... | o_... | f_... | g_... | s | WMS | 2.54 |
| p_... | c_... | o_... | f_... | g_... | s_442151 | WMS | 2.31 |

TABLE 3-continued

Taxonomic Groups with Differential Relative Abundance Between Treatments

| Taxonomic group | | | | | | Association | LDA score |
|---|---|---|---|---|---|---|---|
| p_Firmicutes | .c_Clostridia | o_Clostridiales | | | | WMS | 2.69 |
| p_... | c_... | o_... | f_Lachnospiraceae | | | WMS | 2.69 |
| p_... | c_... | o_... | f_Lachnospiraceae | .g_ | | WMS | 2.44 |
| p_... | c_... | o_... | f_... | .g_... | s_ | WMS | 2.42 |
| p_Firmicutes | .c_Clostridia | .o_Clostridiales | .f_Lachnospiraceae | .g_... | .s_ .190063 | WMS | 2.42 |
| p_... | c_... | o_... | f_Ruminococcaceae | | | WMS | 2.01 |
| p_... | c_... | o_... | f_... | .g_ | | WMS | 2.45 |
| p_... | c_... | o_... | f_... | .g_... | s_ | WMS | 2.40 |
| | | | | | | WMS | 2.40 |

Figure 11A:
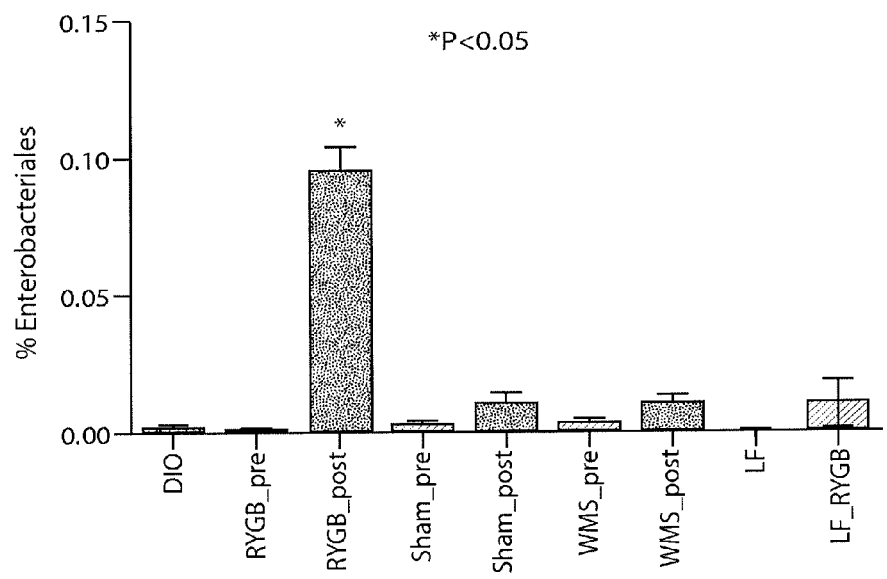
FIG. 11A is a graph showing the relative abundance of Enterobacteriales populations using phylogenetic information from fecal samples taken pre- and post-operative from the RYGB, SHAM, and WMS mice.
Figure 11B:
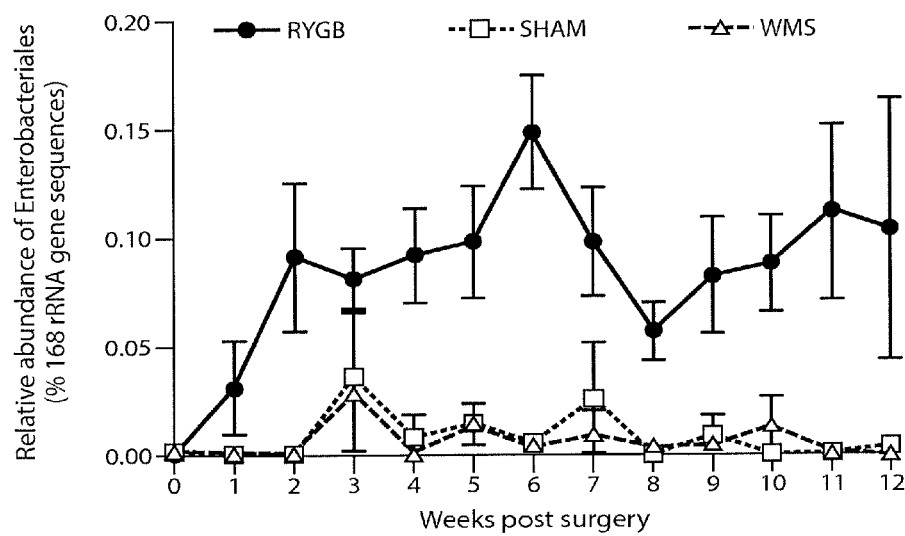
FIG. 11B is a graph showing the relative abundance of Enterobacteriales populations over time of the RYGB, SHAM, and WMS animals after gastric bypass or sham operation as compared to pre-operative abundance.
Figure 11C:
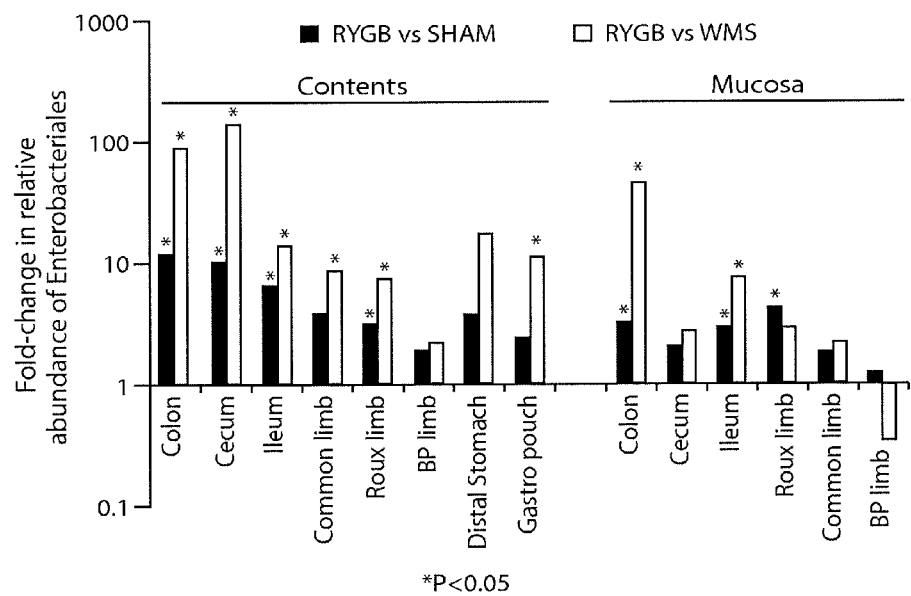
FIG. 11C is a graph showing the mean fold-change of Enterobacteriales comparing RYGB to SHAM and WMS controls along the length of the gastrointestinal tract.

FIG. 11A shows one taxon that demonstrated changes in microbial diversity after RYGB surgery. A percentage change of Enterobacteriales was seen in fecal samples of post surgery RYGB animals. In fact, the percentage of Enterobacteriales taxon present prior to surgery was extremely low in all animals. FIG. 11B shows the relative abundance of Enterobacteriales before and during the 12 weeks following surgery in fecal samples collected from RYGB, SHAM and WMS animals. The relative abundance of Enterobacteriales in RYGB animals increased post surgery and the increased levels were sustained. FIG. 11C shows the relative abundance of luminal contents and mucosa across the length of the gastrointestinal tract, comparing RYGB animals to SHAM and to WMS controls.

Figure 12:
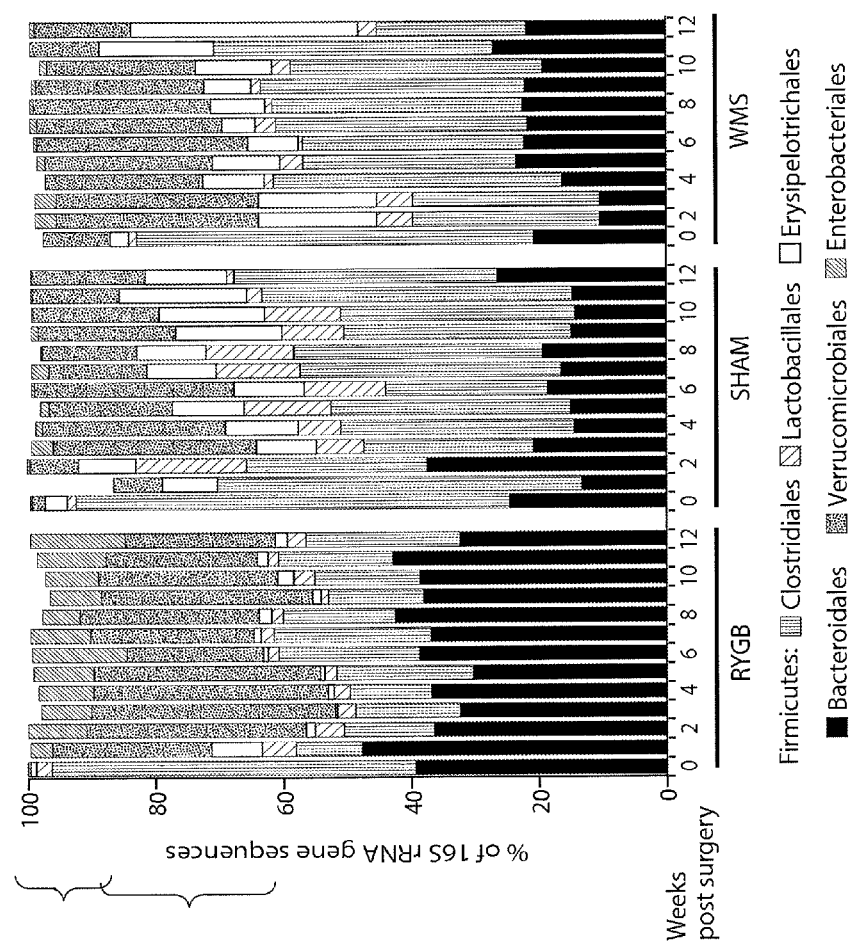
FIG. 12 is a bar graph showing the percentage relative abundance of bacterial orders in RYGB, SHAM, and WMS mice in samples taken before surgery to 12 weeks after surgery, the upper bar highlights the increase in Enterobacteriales populations in RYGB animals and the lower bar highlights the increase in Verrucomicrobiales populations in RYGB animals.
Figure 13:
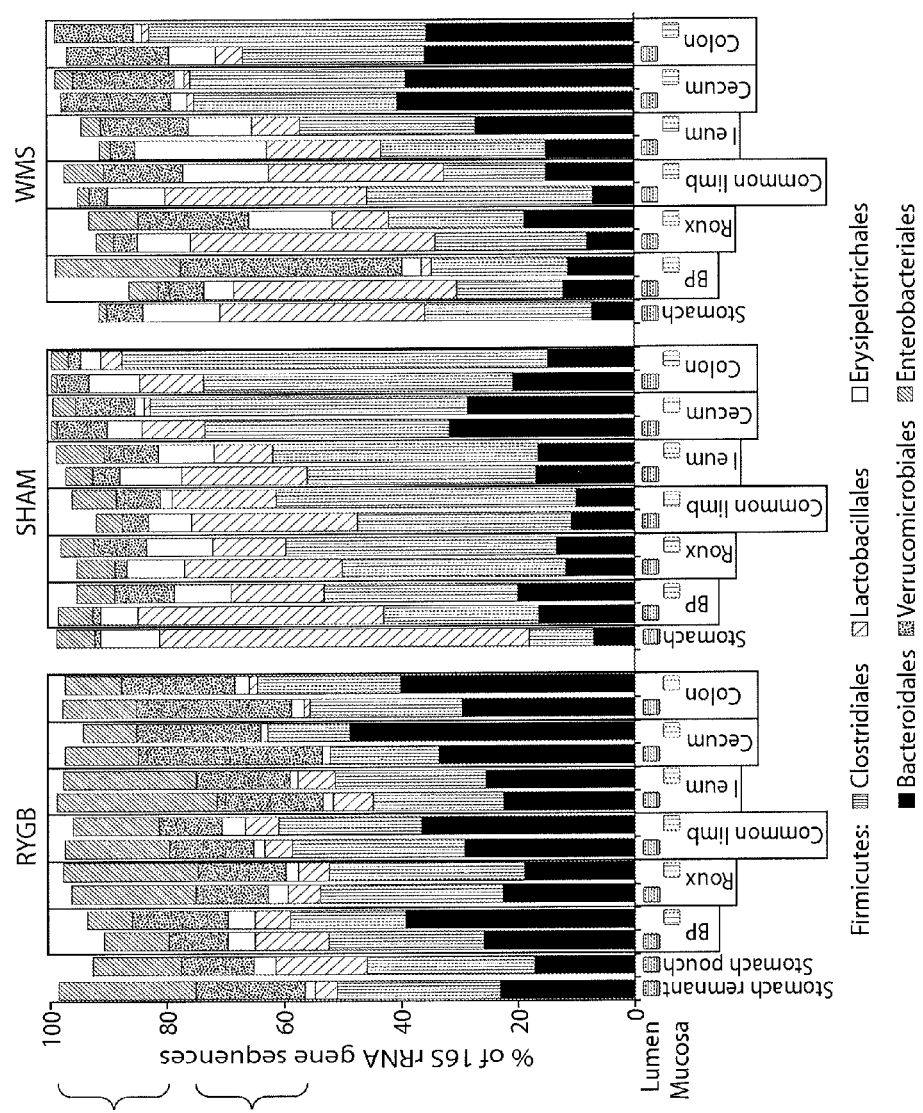
FIG. 13 is a bar graph showing the relative abundance of bacterial orders in RYGB, SHAM, and WMS mice throughout the gastrointestinal tract, the upper bar highlights the increase in Enterobacteriales populations in RYGB animals and the lower bar highlights the increase in Verrucomicrobiales populations in RYGB animals.

FIG. 12 further shows the average relative abundance of bacterial orders in RYGB, SHAM, and WMS mice in fecal samples collected before surgery and every week thereafter until 12 weeks post-surgery. Interestingly, RYGB demonstrated a unique increase and decrease in the prevalence of multiple microbial populations not seen after diet-induced weight loss alone, including an increase in Enterobacteriales, Verrucomicrobiales, and Bacteroidales populations and a decrease in Clostridiales, Lactobacillales, and Erysipelotrichales of the Fimicutes phylum. The increased prevalence of Enterobacteriales, Verrucomicrobiales, and Bacteroidales populations and a decreased abundance of Clostridiales, Lactobacillales, and Erysipelotrichales are also seen in FIG. 13 where the average relative abundance of bacterial orders is analyzed from contents collected from the different gastrointestinal regions: gastric pouch, distal stomach remnant, BP limb, Rx limb, common limb (first 3 cm distal to BP/Rx anastomosis), the distal ileum, ½ cecum, and colon. The WMS mice only exhibited increases in Verrucomicrobiales (e.g., *Akkermansia*) in the mucosal layer, whereas the RYGB mice exhibited increases throughout. See FIG. 13.

Figure 14:
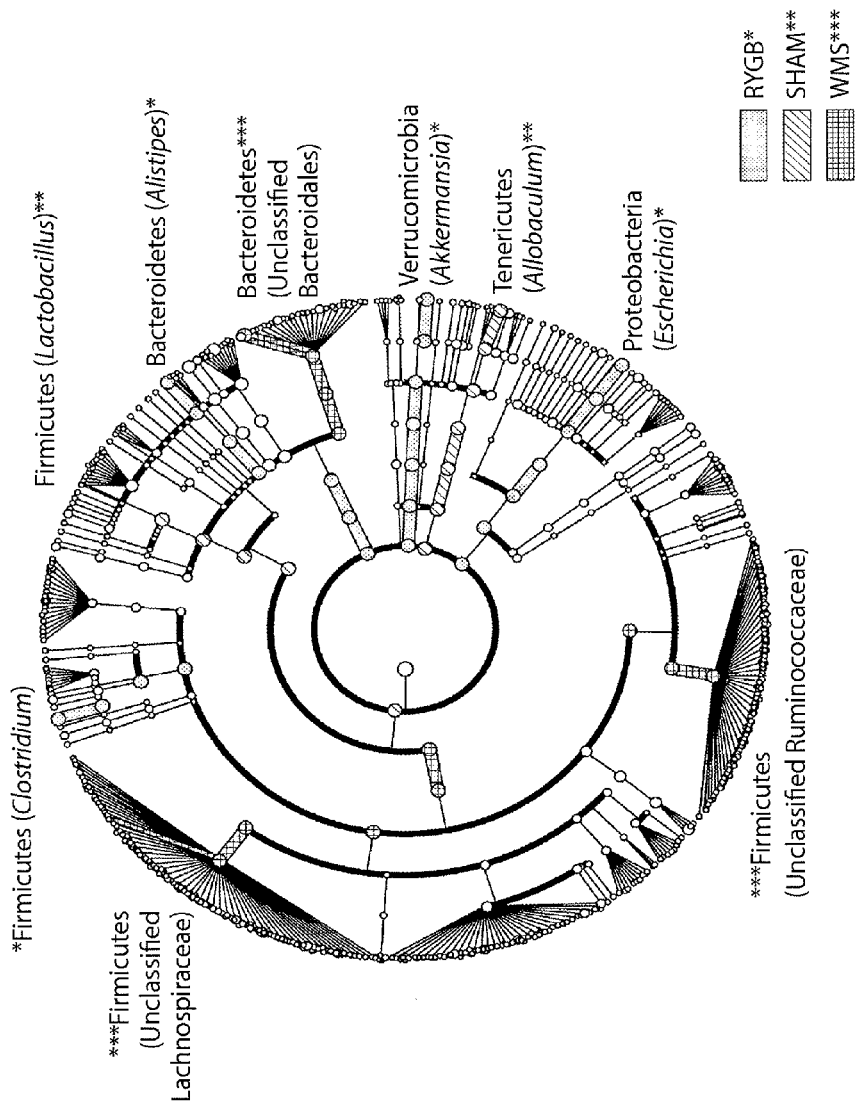
FIG. 14 is a phylogenetic tree depicting nodes within the bacterial taxonomic hierarchy that are significantly enriched in fecal samples from RYGB (*), SHAM (), and WMS (*) mouse fecal samples.

FIG. 14 shows a cladogram depicting the hierarchical structure of relative abundance of microbial taxa present in the fecal samples of RYGB, SHAM, and WMS mice. Prevalence of Bacteroidetes, Verrucomicrobia, Proteobacteria, and Firmicutes phyla in RYGB mice; Firmicutes and Tenericutes in SHAM mice; and Bacteroidetes and Firmicutes in WMS mice is shown. Significant phyla are labeled, followed by the genera in parentheses.

Example 4

Recipient Analysis

Figure 15:
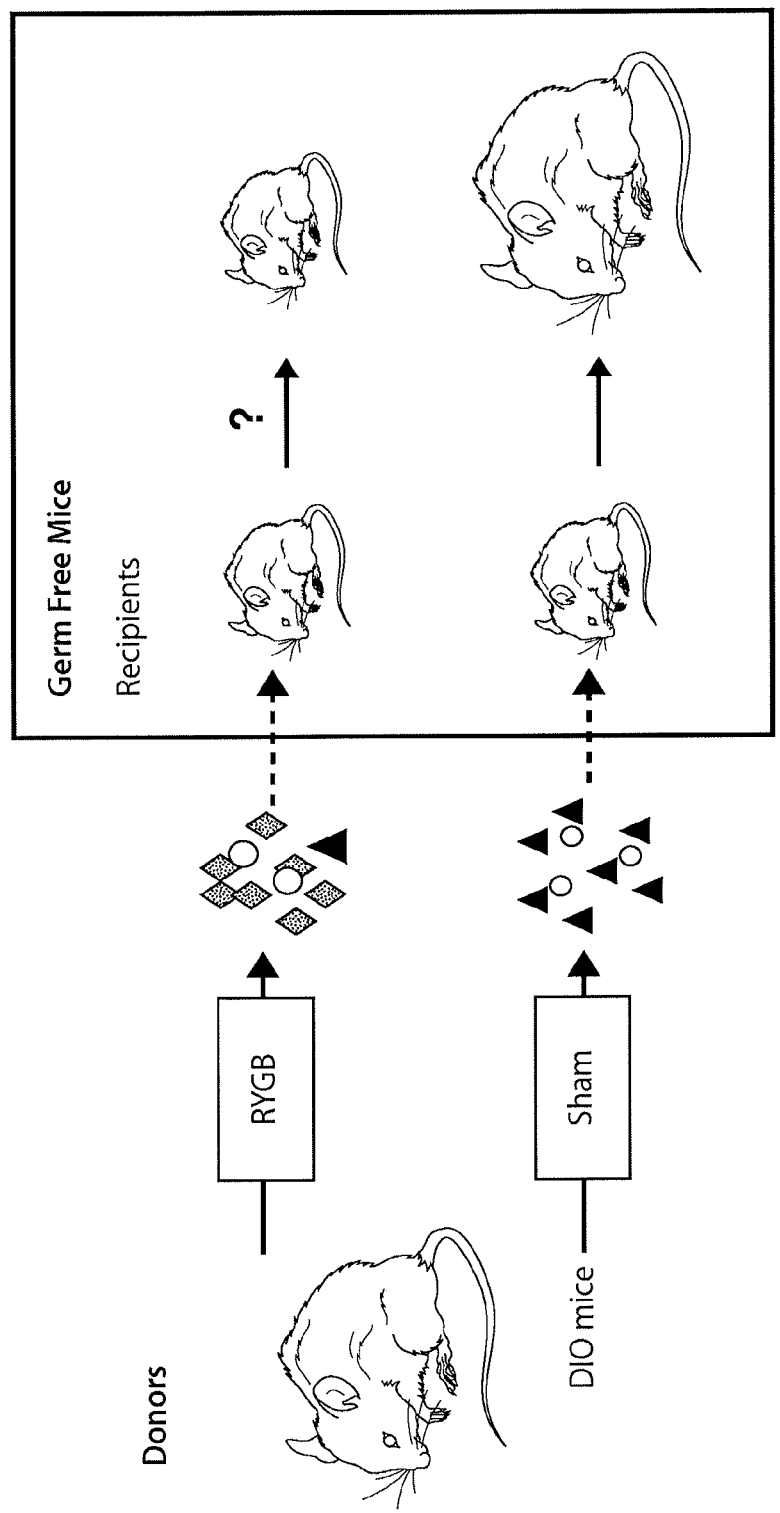
FIG. 15 shows a diagram of the procedure used to generate the recipient animals. In particular, cecal content from RYGB, SHAM, and WMS mice was transferred by oral gavage to germ-free (GF) recipient mice.

Cecal contents from a donor animal of each group, RYGB- and sham-operated (SHAM), were saved and administered by oral gavage to germ-free recipient mice to yield RYGB-R, and SHAM-R mice. Uninnoculated germ-free mice (not shown) were also used as controls. See FIG. 15.

Figure 16:
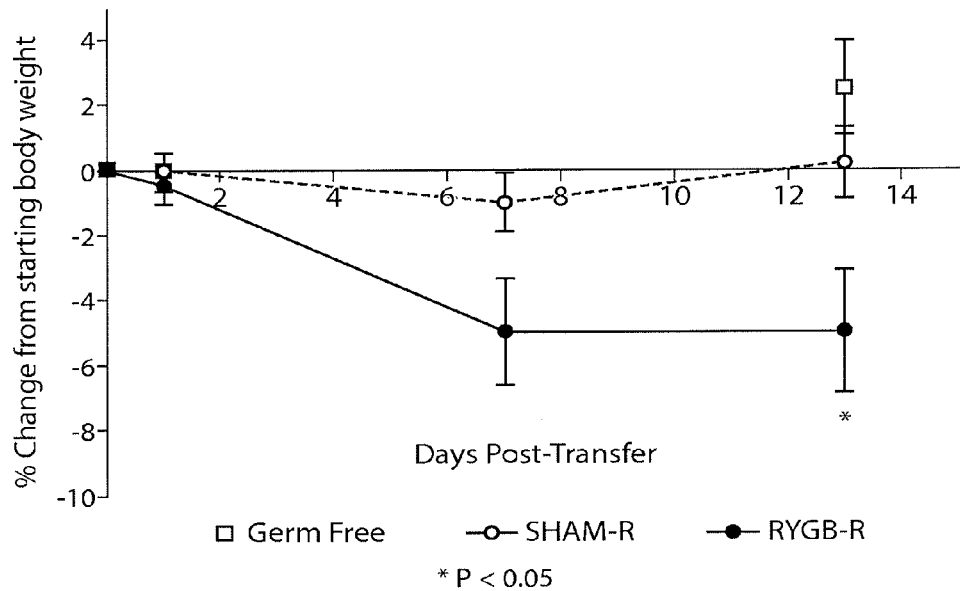
FIG. 16 is a graph of the percentage change in body weights over time after gavage treatment with samples as compared to pre-gavage treatment weights: RYGB-R received cecal contents from RYGB mice, SHAM-R received cecal contents from SHAM mice, and germ-free controls were maintained without exposure to any microbes.
Figure 17:
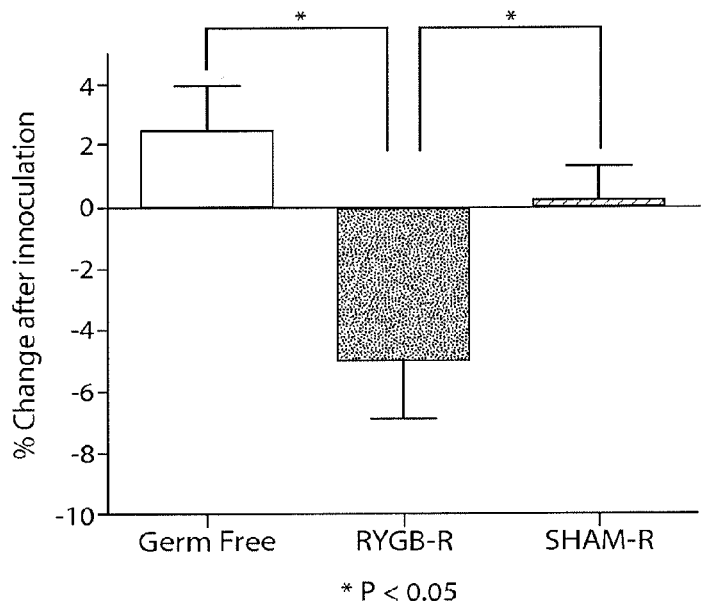
FIG. 17 is a bar graph of the percentage change in body weight of the recipient animals 13 days after gavage treatment as compared to pre-gavage treatment weights.

Animals were weighed prior to microbiota transfer and days 1, 7, and 13 after microbiota transfer, and their weights were compared to pre-gavage treatment weights. FIG. 16 shows the percent change of the weights for the three groups of mice over time, pre-gavage to 13 days post-gavage. The weights in the SHAM-R and germ-free groups demonstrated slight, but non-significant changes from pre-gavage weights. RYGB-R group decreased weights to approximately 5% weight post-gavage. RYGB-R recipients' final weights decreased significantly, whereas both the germ-free and SHAM-R recipients' final weights were not significantly different from their pre-gavage weights (FIG. 17).

Figure 18:
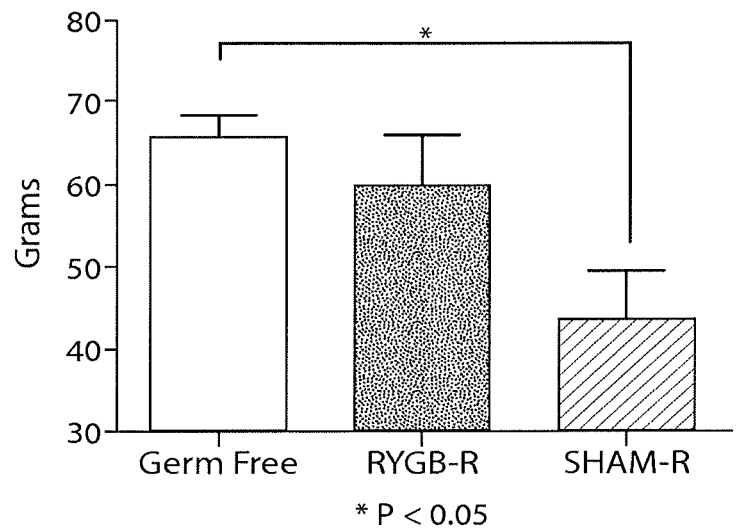
FIG. 18 is a bar graph showing the cumulative food intake of animals gavage treated with samples from RYGB (RYGB-R), SHAM (SHAM-R), or control (germ-free)

Recipient animals were housed individually on wire floors to weigh food intake at day 0, 7, and 13 after colonization. FIG. 18 shows total food intake during the 2 week colonization of the three groups. Food intake in the RYGB-R group was not significantly different from the germ-free group, while the SHAM-R group ate significantly less than the GF group.

TABLE 4

Effect of transferred microbiota on glucose metabolism and fat content.

| | RYGB-R | SHAM-R | GF |
|---|---|---|---|
| N | 15 | 10 | 7 |
| Fasted blood glucose (mg/dL) | $148 \pm 5.5^A$ | $147 \pm 7.4^A$ | $120 \pm 3.9^B$ |
| Fasted insulin (ng/mL) | $0.46 \pm 0.10^A$ | $0.99 \pm 0.19^A$ | $0.73 \pm 0.19^A$ |
| HOMA-IR | $4.4 \pm 0.98^A$ | $9.8 \pm 4.1^A$ | $5.5 \pm 1.5^A$ |
| Fat pad weight (g) | $0.86 \pm 0.11^A$ | $1.49 \pm 0.11^B$ | $0.96 \pm 0.11^A$ |
| Fat pad weight (% body weight) | $2.5 \pm 0.30^A$ | $3.9 \pm 0.27^B$ | $2.8 \pm 0.32^A$ |

Values are represented as means ± SEM.
Data not annotated by the same letter are significantly different (P < 0.05, ANOVA).

Figure 19:
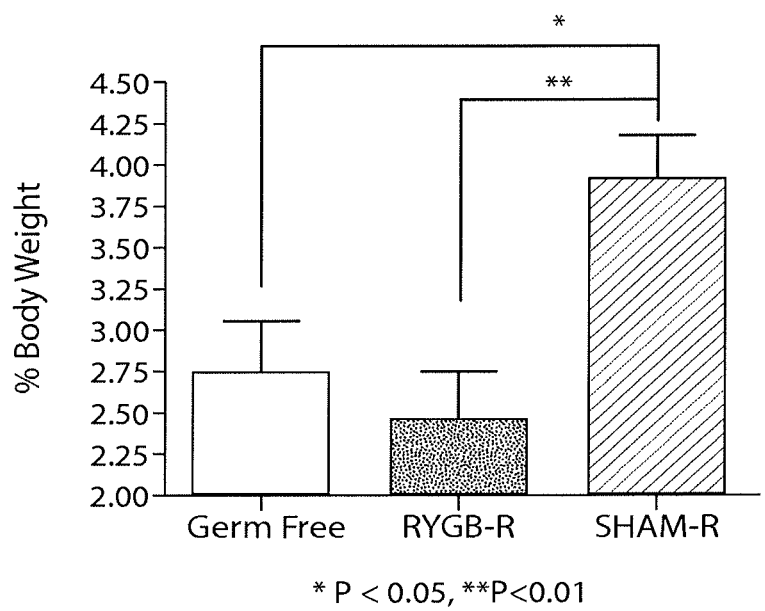
FIG. 19 is a bar graph showing the adiposity index of the recipient mice. In particular, decreased adiposity was transmissible via the gut microbiota from RYGB mice.
Figure 20:
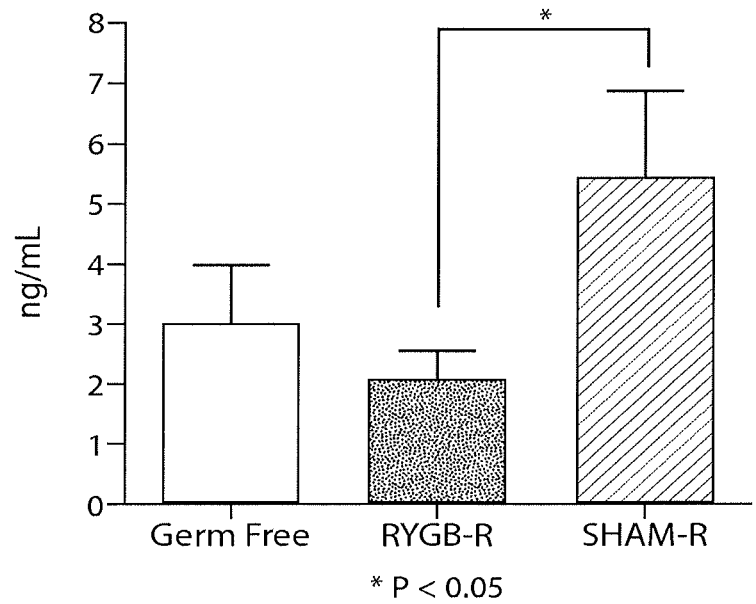
FIG. 20 is a bar graph showing leptin levels in recipient animals at time of tissue harvest.

As shown in Table 4, the recipients of microbiota from RYGB donors had decreased fat pad weight. The adiposity index was determined from epididymal and retroperitoneal fat pads collected from the recipient animals of the three groups. Both germ-free and RYGB-R recipients had significantly lower percentage of adiposity than the SHAM-R group. See FIG. 19. In addition, there is a trend towards improvement in insulin sensitivity in the RYGB-R group relative to the SHAM-R group, as indicated by homeostatic model assessment for insulin resistance (HOMA-IR). Plasma leptin levels taken at end of study from recipient animals colonized with cecal contents from RYGB or SHAM operated donors are shown in FIG. 20. Leptin levels appear to be correlated with adiposity index of recipient animals.

Figure 21:
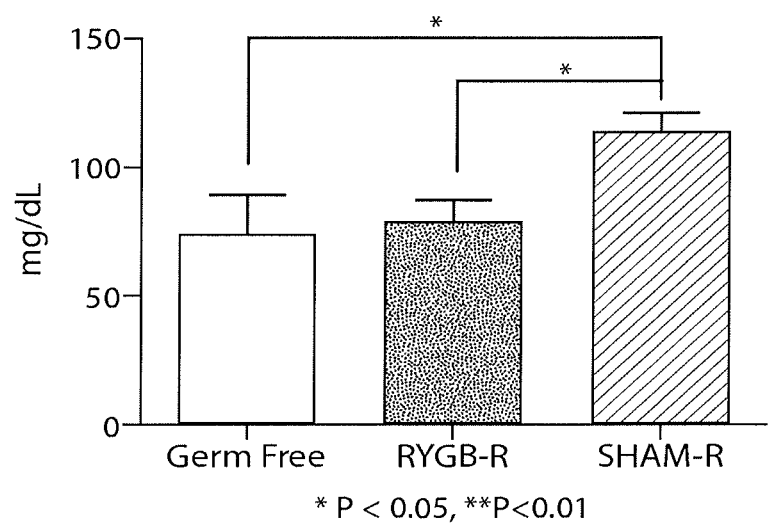
FIG. 21 is a bar graph showing the level of serum triglycerides in recipient animals measured at the time of tissue harvest.

Serum triglyceride levels were measured in serum from recipients of each group. Like the donor animals shown in FIG. 5, SHAM-R animals had higher triglycerides than RYGB-R and germ-free animals. See FIG. 21.

Figure 22A:
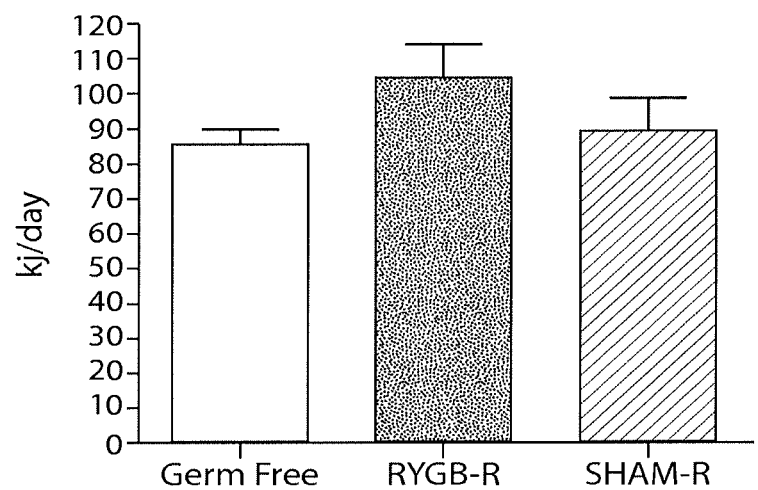
FIG. 22A is a bar graph showing the level of energy expenditure of animals gavage-treated with samples from RYGB (RYGB-R), SHAM (SHAM-R), or control (GF) 5 days post-injection with doubly labeled water.
Figure 22B:
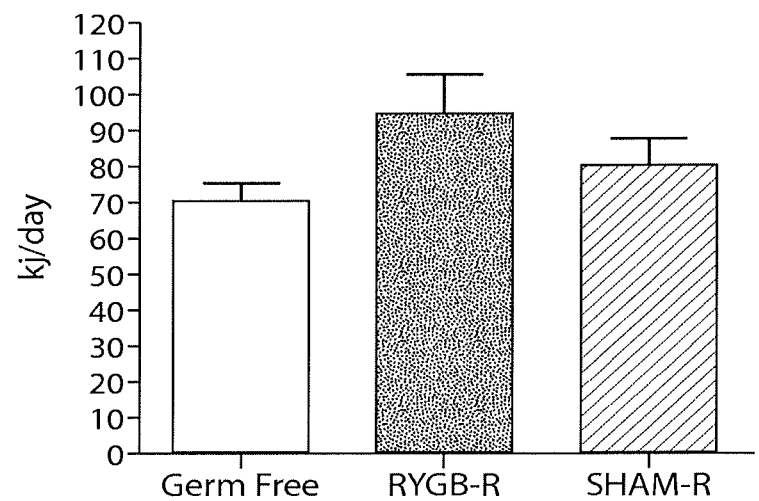
FIG. 22B is a bar graph showing the level of energy expenditure of animals gavage-treated with samples from RYGB (RYGB-R), SHAM (SHAM-R), or control (GF) 8 days post-injection with doubly labeled water.
Figure 23A:
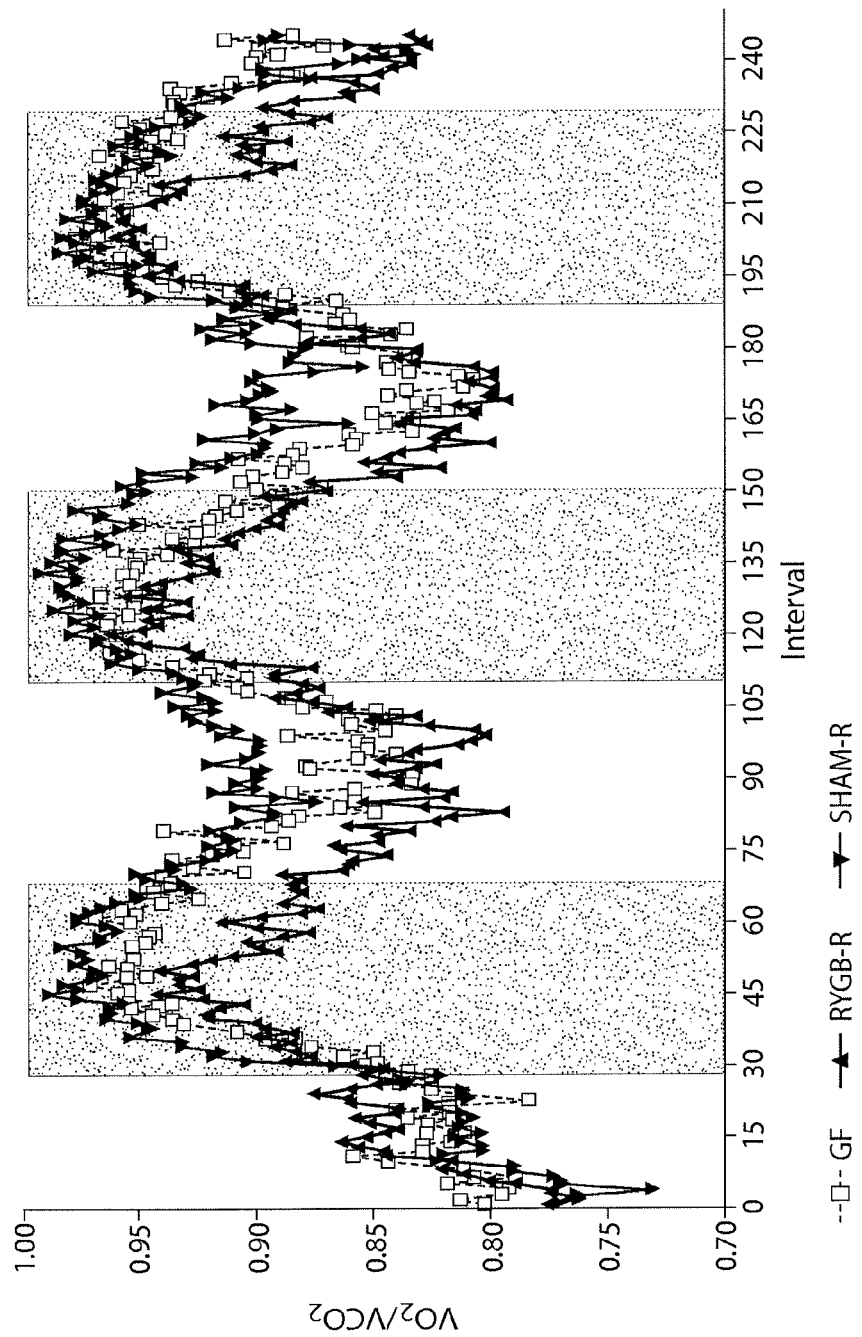
FIG. 23A is a 72 hour time course graph of the respiratory quotient measured by indirect calorimetry of recipient animals 2 weeks following gavage with cecal samples from RYGB (RYGB-R), SHAM (SHAM-R), or control (GF)
Figure 23B:
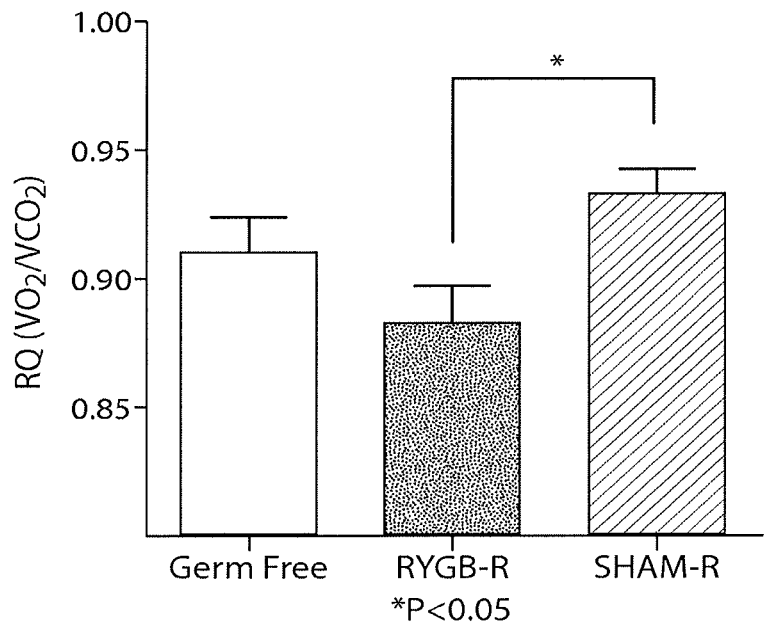
FIG. 23B is a graph showing the overall difference in respiratory quotient between RYGB-R, SHAM-R, and GF groups from FIG. 24A.
Figure 23C:
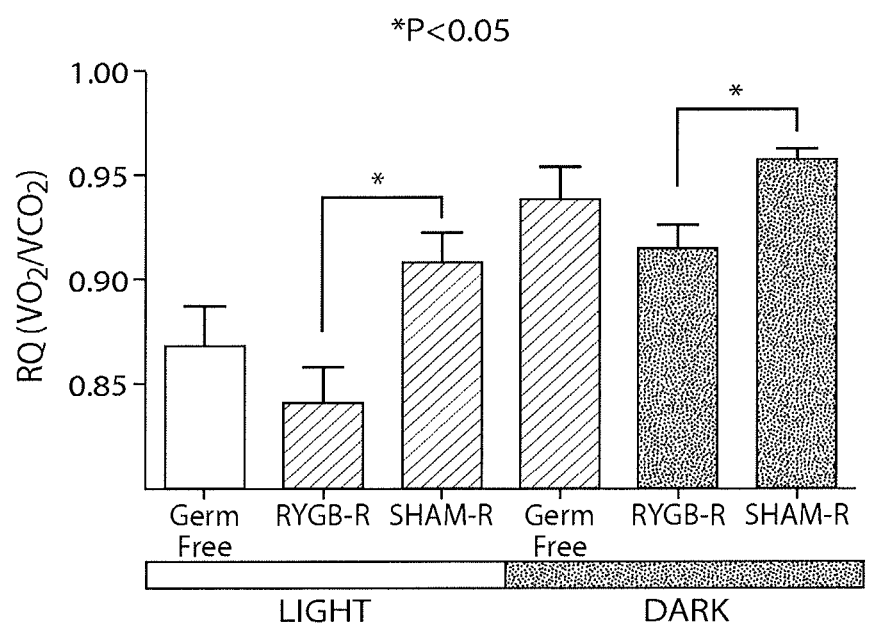
FIG. 23C is the average difference in respiratory quotient during the light cycles and the dark cycles among each recipient group.

Energy expenditure was measured via doubly labeled water in recipients of each group. RYGB-R animals exhibited a non-significant trend towards higher energy expenditure than SHAM-R and germ-free animals. See FIGS. 22A and 22B. The respiratory quotient (RQ), or respiratory exchange ratio, was calculated as $VCO_2/VO_2$ as an indicator of substrate oxidation for fuel. FIGS. 23A and 23B show an overall lower RQ value in recipient animals two weeks following colonization with RYGB microbiota as compared with RQ values of recipient animals colonized with SHAM microbiota. FIG. 23C shows that the RQ differences are significant during both light and dark periods, with a greater fold drop in RQ in the light period. Together, FIGS. 23A-C demonstrate a preference for lipid oxidation in RYGB-R animals as compared with SHAM-R animals, particularly during the light phase of the daily light-dark cycles.

Figure 24A:
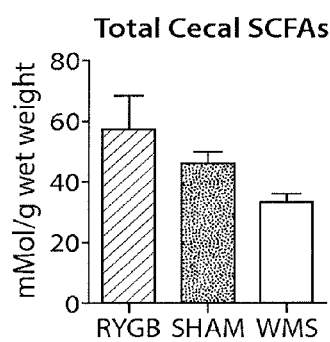
FIG. 24A is a bar graph of the total cecal SCFAs of each donor group.
Figure 24B:
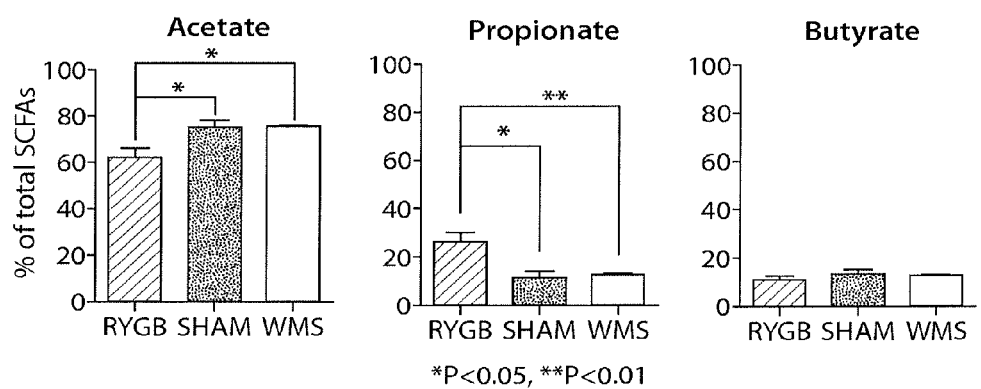
FIG. 24B is a series of graphs showing acetate, propionate, and butyrate as a percentage of total SCFAs in the donor groups.
Figure 24C:
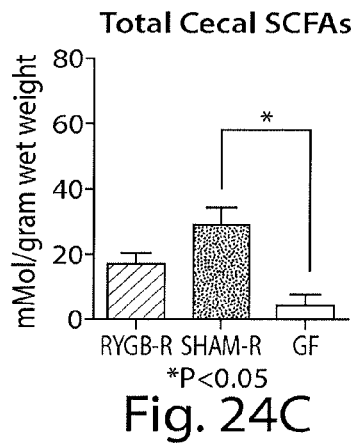
FIG. 24C is a bar graph of the total cecal SCFAs of each recipient group.
Figure 24D:
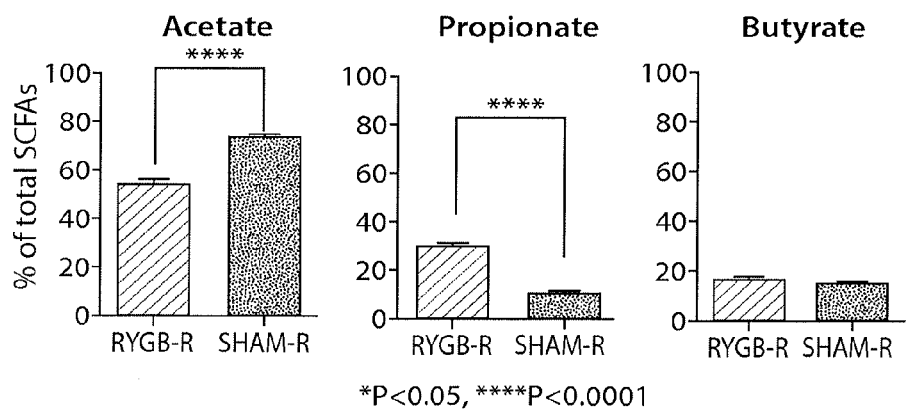
FIG. 24D is a series of graphs showing acetate, propionate, and butyrate as a percentage of total SCFAs in the recipient groups.

Cecal short chain fatty acid (SCFA) composition was measured in both donor and recipient animals. See FIGS. 24A-D. Total cecal SCFAs (FIGS. 24A and 24C) and percentage of total SCFAs that were acetate, propionate, and butyrate (FIGS. 24B and 24D) were measured. See FIGS. 24A-D. The relative proportion of acetate, propionate and butyrate levels were maintained in both donor and recipient groups with increased propionate production and decreased acetate production. In the recipient group, SHAM-R animals produced significantly more SCFAs than germ-free animals, and RYGB-R produced an intermediate quantity. The difference is not as apparent in the donor group.

Example 5

Recipient Microbiota Profiles

Fecal samples were collected post-gavage from recipient animals of the RYGB cecal content, SHAM cecal content or WMS cecal content at intervals of 1, 2, 3, 7, and 13 days to determine the sustainability of the microbial diversity from the transferred cecal contents within the un-operated, normal gastrointestinal anatomy of recipient animals.

Figure 25:
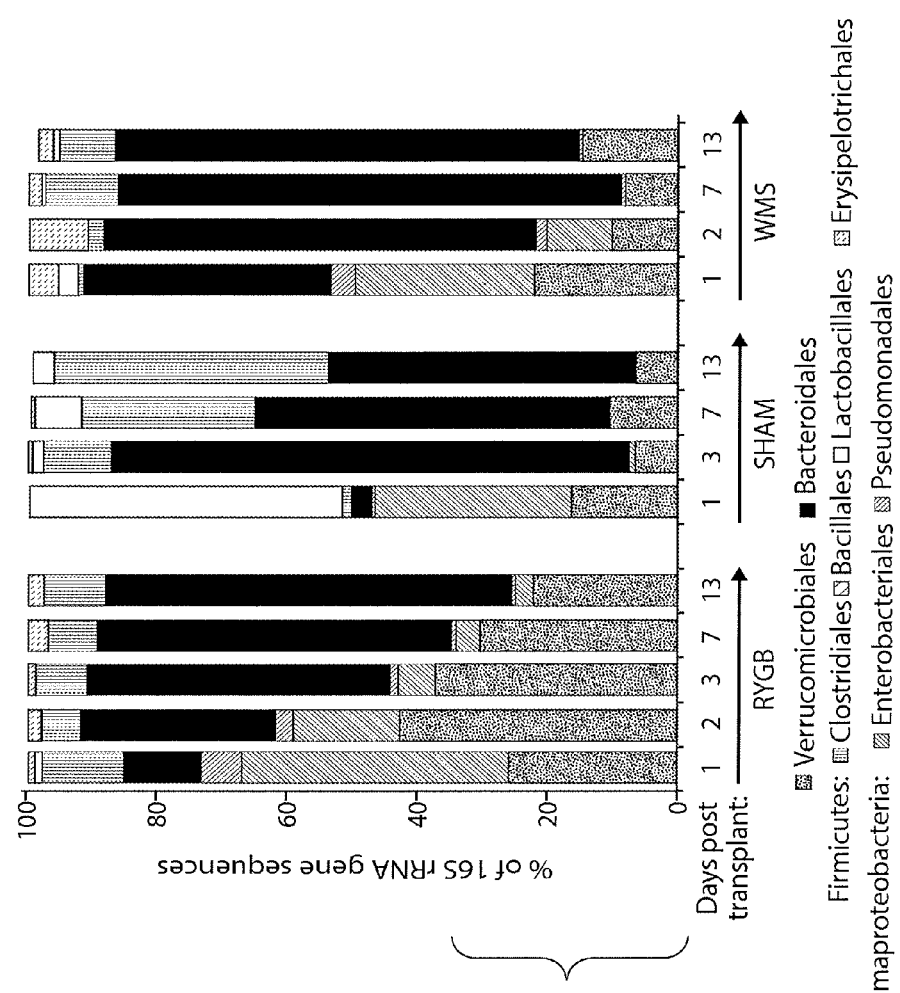
FIG. 25 is a bar graph showing the relative abundance of bacterial orders in recipient animals following gavage with samples of RYGB, SHAM, or WMS cecal content, the bar highlights the increase in Verrucomicrobiales populations in RYGB animals.

The microbial diversity was compared in samples of isolated bacterial DNA of fecal samples collected from RYGB-R, SHAM-R and WMS-R recipient animals. FIG. 25 shows the relative abundance of bacterial orders. Unlike the increase in Enterobacteriales in the RYGB animals in FIG. 12, the RYGB-R experimental groups demonstrated a reduced abundance of this particular order of bacteria by the end of the colonization period. Interestingly, the increased abundance of the Verrucomicrobiales group is sustained throughout the colonization period, which is unique compared to the SHAM-R and WMS-R samples. Table 5 shows an overall significant increase in *Alistipes* and *Akkermansia* throughout the gastrointestinal tract of the RYGB-R group.

TABLE 5

Taxonomic Groups with Differential Relative Abundance Between Recipients

| | | Taxonomic group | | | | | Association | LDA score |
|---|---|---|---|---|---|---|---|---|
| p_Bacteroidetes | c_Bacteroidia | o_Bacteroidales | .f_... | | | | RYGB | 2.87 |
| p_... | c_... | o_... | f_... | g_... | | | RYGB | 2.87 |
| p_... | c_... | o_... | f_... | g_... | | | RYGB | 2.87 |
| p_... | c_... | o_... | f_Rikenellaceae | | | | RYGB | 2.39 |
| p_... | c_... | o_... | f_... | g_Alistipes | | | RYGB | 2.39 |
| p_... | c_... | o_... | f_... | g_... | s_Alistipesfinegoldii | | RYGB | 2.42 |
| p_... | c_... | o_... | f_... | g_... | s_Alistipesfinegoldii.109956 | | RYGB | 2.42 |
| p_Firmicutes | .c_Clostridia | .o_Clostridiales | .f_Clostridiaceae | | | | RYGB | 2.23 |
| p_... | c_... | o_... | f_... | g_Clostridium | | | RYGB | 2.22 |
| p_Proteobacteria | c_Gammaproteobacteria | o_Enterobacteriales | f_Enterobacteriaceae | | | | RYGB | 2.74 |
| p_... | c_... | o_... | f_... | | | | RYGB | 2.67 |
| p_Verrucomicrobia | c_Verrucomicrobiae | o_Verrucomicrobiales | f_Verrucomicrobiaceae | | | | RYGB | 2.67 |
| p_... | c_... | o_... | f_... | | | | RYGB | 3.03 |
| p_... | c_... | o_... | f_... | g_Akkermansia | | | RYGB | 3.03 |
| p_... | c_... | o_... | f_... | g_... | s | | RYGB | 3.03 |
| p_... | c_... | o_... | f_... | g_... | s_178399 | | RYGB | 3.03 |
| p_Bacteroidetes | .c_Bacteroidia | .o_Bacteroidales | .f_Porphyromonadaceae | | | | RYGB | 3.03 |
| p_... | c_... | o_... | f_... | g_Parabacteroides | | | RYGB | 3.04 |
| p_... | c_... | o_... | f_... | g_... | s_234036 | | RYGB | 2.98 |
| p_... | c_... | o_... | f_... | g_... | s | | SHAM | 2.98 |
| p_... | c_... | o_... | f_... | g_... | s_249661 | | SHAM | 2.98 |
| p_Firmicutes | c_Bacilli | o_Lactobacillales | f_Lactobacillaceae | | | | SHAM | 3.11 |
| p_... | c_... | o_... | f_... | g_Lactobacillus | | | SHAM | 2.73 |
| p_... | c_... | o_... | f_... | g_... | s | | SHAM | 2.25 |
| p_Firmicutes | .c_Bacilli | .o_Lactobacillales | .f_Lactobacillaceae | .g_Lactobacillus | .s_323257 | | SHAM | 2.25 |
| p_Firmicutes | .c_Clostridia | o_Clostridiales | f_Lachnospiraceae | | | | SHAM | 2.25 |
| p_... | c_... | o_... | f_... | g_... | | | SHAM | 2.91 |
| p_... | c_... | o_... | f_... | g_... | | | SHAM | 2.85 |
| p_... | c_... | o_... | f_... | g_... | .s | | SHAM | 2.83 |
| p_... | c_... | o_... | f_... | g_... | s_136452 | | SHAM | 2.83 |
| p_Proteobacteria | .c_Gammaproteobacteria | .o_Enterobacteriales | .f_Enterobacteriaceae | | | | SHAM | 2.85 |
| p_... | c_... | o_... | f_... | g_Erwinia | | | SHAM | 2.39 |
| p_... | c_... | o_... | f_... | g_... | s | | SHAM | 2.39 |
| p_... | c_... | o_... | f_... | g_... | s_9822 | | SHAM | 2.39 |

TABLE 5-continued

Taxonomic Groups with Differential Relative Abundance Between Recipients

| | | Taxonomic group | | | | | Association | LDA score |
|---|---|---|---|---|---|---|---|---|
| p_Bacteroidetes | c_Bacteroidia | o_Bacteroidales | f_... | g_... | s_183770 | | WMS | 2.49 |
| p_... | c_... | o_... | f_... | g_... | s_206324 | | WMS | 2.03 |
| p_... | c_... | o_... | f_... | g_... | s_442151 | | WMS | 2.65 |
| p_... | c_... | o_... | f_Bacteroidaceae | g_... | | | WMS | 3.23 |
| p_... | c_... | o_... | f_... | g_Bacteroides | | | WMS | 3.23 |
| p_... | c_... | o_... | f_... | g_... | s | | WMS | 3.19 |
| p_... | c_... | o_... | f_... | g_... | s_348374 | | WMS | 2.26 |
| p_Proteobacteria | c_Gammaproteobacteria | o_Enterobacteriales | f_Enterobacteriaceae | g_Escherichia | s_86458 | | WMS | 2.68 |
| p_... | c_... | o_... | f_... | g_... | s | | WMS | 2.68 |
| p_... | c_... | o_... | f_... | g_... | s_169182 | | WMS | 2.26 |
| p_Tenericutes | c_Erysipelotrichi | o_Erysipelotrichales | f_Erysipelotrichaceae | | | | WMS | 2.26 |
| p_... | c_... | o_... | f_... | g_Allobaculum | | | WMS | 2.26 |
| p_... | c_... | o_... | f_... | g_... | | | WMS | 2.28 |
| p_... | c_... | o_... | f_... | g_... | s | | WMS | 2.28 |
| p_... | c_... | o_... | f_... | g_... | s_227728 | | WMS | 2.28 |

What is claimed is:

1. A method of altering relative abundance of microbiota in a subject comprising administering to the subject an effective dose of a composition consisting essentially of substantially purified Verrucomicrobia; wherein the subject has a disorder selected from the group consisting of: obesity, metabolic syndrome, insulin deficiency, insulin-resistance related disorders, glucose intolerance, diabetes, non-alcoholic fatty liver, and abnormal lipid metabolism.

2. The method of claim 1, wherein the substantially purified Verrucomicrobia is substantially purified Verrucomicrobiales.

3. The method of claim 2, wherein upon administration of the substantially purified Verrucomicrobiales the relative abundance of Verrucomicrobiales is increased in the subject by at least about 5%.

4. The method of claim 1, wherein the step of administering the composition comprises delivering the composition to at least a stomach, a small intestine, and a large intestine of the subject.

5. The method of claim 1, wherein the substantially purified Verrucomicrobia is a live bacterial strain.

6. The method of claim 1, further comprising administering an antibiotic and/or an osmotic laxative to the subject.

7. The method of claim 1, wherein the relative abundance of Firmicutes, Tenericutes, or Erysipelotrichales is decreased at least about 5%.

8. The method of claim 1, further comprising performing a surgical procedure selected from the group consisting of: gastric bypass, duodenojejunal bypass, biliopancreatic diversion, vertical sleeve gastrectomy, adjustable gastric banding, vertical banded gastroplasty, intragastric balloon therapy, gastric plication, Magenstrasse and Mill, small bowel transposition, biliary diversion, and duodenal endoluminal barrier.

9. The method of claim 1, wherein the composition is administered orally.

10. The method of claim 1, wherein the effective dose of the composition is administered before, concurrent with, or after a treatment with a composition or agent for bile acid modulation.

11. A method of treating obesity in a subject in need of the treatment, comprising administering a first effective dose of a composition comprising substantially purified Verrucomicrobia for increasing relative abundance of microbiota comprising Verrucomicrobia, Bacteroidetes, Proteobacteria and Firmicutes in a gastrointestinal tract of the subject in need thereof by at least about 5%.

12. The method of claim 11, wherein the relative abundance of at least one of Verrucomicrobiales, Bacteroidales, Enterobacteriales, or Clostridia is increased by at least about 5%.

13. The method of claim 11, wherein the relative abundance of at least one of Enterobacteriaceae, Rikenellaceae, Clostridiaceae, or Verrucomicrobiaceae is increased by at least about 5%.

14. The method of claim 11, further comprising performing a surgical procedure selected from the group consisting of: gastric bypass, biliopancreatic diversion, vertical sleeve gastrectomy, adjustable gastric banding, vertical banded gastroplasty, intragastric balloon therapy, gastric plication, Magenstrasse and Mill, small bowel transposition, biliary diversion, and duodenal endoluminal barrier.

15. The method of claim 11, further comprising administering an antibiotic to the subject.

16. The method of claim 11, further comprising administering a compound to alter at least one of Bacteroidetes, Verrucomicrobia, Firmicutes, Tenericutes and Proteobacteria.

17. A method of altering microbiota in a subject comprising: administering an effective dose of a composition comprising substantially purified Verrucomicrobia to the subject, thereby altering abundance of one or more microbiota in the subject so that the microbiota mimics a microbiota found in a subject responsive to a gastric bypass or other gastrointestinal bariatric or metabolic procedure; wherein the subject has a disorder selected from obesity, metabolic syndrome, insulin deficiency, insulin-resistance related disorders, glucose intolerance, diabetes, non-alcoholic fatty liver, and abnormal lipid metabolism.

18. The method of claim 17, wherein the composition alters at least one phylum or order selected from Bacteroidetes, Verrucomicrobia, Firmicutes, Tenericutes and Proteobacteria.

19. The method of claim 18, wherein the administering the composition results in decrease of the relative abundance of at least one of Firmicutes, Tenericutes and Erysipelotrichales by at least about 5%.

20. The method of claim 17, wherein the composition further comprises a compound that alters at least one of Bacteroidetes, Verrucomicrobia, Firmicutes, Tenericutes and Proteobacteria.

21. The method of claim 17, wherein the effective dose of the composition is administered before, concurrent with, or after a treatment with a composition or agent for bile acid modulation.

22. A method of altering metabolic function in a subject, comprising administering an effective dose of a composition comprising substantially purified Verrucomicrobia, thereby
    increasing the relative abundance of propionate-producing bacteria in a gastrointestinal tract of the subject by at least about 5%;
    reducing acetate in a gastrointestinal tract of the subject; and
    altering a ratio of short chain fatty acids in a gastrointestinal tract of the subject; wherein the metabolic function is increased.

23. The method of claim 22, wherein the propionate-producing bacteria is *Escherichia coli*.

24. The method of claim 22, wherein the ratio of short chain fatty acids is altered by manipulating bacteria in a gastrointestinal tract of the subject.

25. The method of claim 22, wherein the ratio of short chain fatty acids is altered by creating and using bacteria to alter a ratio of short chain fatty acids in an environment.

26. The method of claim 22, wherein the ratio of short chain fatty acids is altered by administering a cocktail of one or more short chain fatty acids to the subject.

27. The method of claim 22, wherein metabolic function is determined by measuring body weight, food intake, or energy expenditure.

28. The method of claim 22, wherein metabolic function is determined by measuring glucose metabolism, including insulin production or secretion, or insulin sensitivity.

29. The method of claim 22, wherein the effective dose of the composition is administered before, concurrent with, or after a treatment with a composition or agent for bile acid modulation.

* * * * *